(12) United States Patent
Salonen et al.

(10) Patent No.: US 7,901,885 B2
(45) Date of Patent: Mar. 8, 2011

(54) GENES AND MARKERS IN TYPE 2 DIABETES AND OBESITY

(75) Inventors: Jukka T. Salonen, Kuopio (FI); Jelena Hyppönen, Kuopio (FI); Jari Kaikkonen, Kuopio (FI); Mia Pirskanen, Kuopio (FI); Pekka Uimari, Kuopio (FI); Juha-Matti Aalto, Siilinjärvi (FI)

(73) Assignee: DSM IP Assets B.V., Heerlen (NL)

( * ) Notice: Subject to any disclaimer, the term of this patent is extended or adjusted under 35 U.S.C. 154(b) by 509 days.

(21) Appl. No.: 11/798,002

(22) Filed: May 9, 2007

(65) Prior Publication Data

US 2007/0292412 A1    Dec. 20, 2007

Related U.S. Application Data

(60) Provisional application No. 60/864,681, filed on Nov. 7, 2006, provisional application No. 60/863,438, filed on Oct. 30, 2006, provisional application No. 60/827,306, filed on Sep. 28, 2006, provisional application No. 60/819,015, filed on Jul. 7, 2006, provisional application No. 60/805,522, filed on Jun. 22, 2006, provisional application No. 60/798,774, filed on May 9, 2006, provisional application No. 60/798,706, filed on May 9, 2006.

(51) Int. Cl.
*C12Q 1/68*    (2006.01)
*C12P 19/34*    (2006.01)

(52) U.S. Cl. .................. 435/6; 435/91.1; 436/63

(58) Field of Classification Search .............. None
See application file for complete search history.

(56) References Cited

U.S. PATENT DOCUMENTS

| | | | |
|---|---|---|---|
| 6,638,721 | B2 | 10/2003 | Meyers et al. |
| 6,686,176 | B2 | 2/2004 | Beasley et al. |
| 2003/0092019 | A1 * | 5/2003 | Meyer et al. ............ 435/6 |
| 2004/0156854 | A1 | 8/2004 | Mulligan et al. |

FOREIGN PATENT DOCUMENTS

| | | |
|---|---|---|
| WO | WO-02/33056 A2 | 4/2002 |
| WO | WO-2004/006838 A2 | 1/2004 |
| WO | WO-2004/063218 A1 | 7/2004 |

OTHER PUBLICATIONS

Ioannidis (Nature Genetics, vol. 29, pp. 306-309, Nov. 2001).*
Hirschhorn et al. (Genetics in Medicine. vol. 4, No. 2, pp. 45-61, Mar. 2002).*
Barroso et al. (Diabetic Medicine 2005, 22 :517-535).*
Mummidi (J Biol Chem, 2002, 275: 18946-18961).*
Database SNP (Online), Aug. 20, 2004, "Submitted SNP (ss) Report/ ss23763128" retrieved from NCBI. Database accession No. ss23763128.
Database SNP (Online), Jul. 19, 2005, "Submitted SNP (ss) Report/ ss44752597" retrieved from NCBI, Database accession No. ss44752597.
Database SNP (Online), Aug. 20, 2004, "Submitted SNP (ss) Report/ ss23763076" retrieved from NCBI. Database accession No. 23763076.
Database SNP (Online), Jul. 15, 2005, "Submitted SNO (ss) Report/ ss38534782" retrieved from NCBI. Database accession No. ss38534782.
Database SNP (Online), Feb. 12, 2003, "Submitted SNP (ss) Report/ ss6743360" retrieved from NCBI. Database accession No. ss6743360.
Prior et al., Diabetologia, Aug. 2005, vol. 48, Supplement 1, p. A143.

* cited by examiner

*Primary Examiner* — Sarae Bausch
(74) *Attorney, Agent, or Firm* — Birch, Stewart, Kolasch & Birch, LLP

(57) ABSTRACT

Genes, SNP markers and haplotypes of susceptibility or predisposition to T2D and subdiagnosis of T2D and related medical conditions are disclosed. Methods for diagnosis, prediction of clinical course and efficacy of treatments for T2D, obesity and related phenotypes using polymorphisms in the risk genes are also disclosed. The genes, gene products and agents of the invention are also useful for monitoring the effectiveness of prevention and treatment of T2D and related traits. Kits are also provided for the diagnosis, selecting treatment and assessing prognosis of T2D. Novel methods for prevention and treatment of metabolic diseases such as T2D based on the disclosed T2D genes, polypeptides and related pathways are also disclosed.

3 Claims, No Drawings

```
                         SEQUENCE LISTING

<160> NUMBER OF SEQ ID NOS: 1

<210> SEQ ID NO 1
<211> LENGTH: 1401
<212> TYPE: DNA
<213> ORGANISM: Homo sapiens

<400> SEQUENCE: 1
gcaatgggta aagtctttta aaaaattaag gcattatgaa agatagttat ggaaagataa      60
ttttagcaca gcagagacag aggacttaga gactgaacac tgaggtcaat agcaacaatt     120
taagcaaaga gtaatagggc ttgaattaaa gcaaacgcaa tagagaggac gtgacaaaac     180
tgtgagcctt ttaggaggga gaattggcag actttagtgc tagtttrgatg tgaaagaaat     240 gatgggaaag aaagaagaga tgaacaccac tctgagtttt cagcttggga gatggtggat     300
aaggatgcca ttaaaatata tgtaagagaa ttaaaagagg aaaacaaaat ttaaggaggt     360
gggtaagttt ggtttttggat ttgaggtggc aatgggccat tcaaatggaa acgtgtaata     420
ggaagtcaaa ttcataaaaa aggtgtgcgc tagaagtcat tagcatatca gcaagagtca     480
aagctgggaa aggtaagaga aactaggata agcatataaa accaggagat gatcagctaa     540
aggatcctgg ggataaaaca tatagacgat cggcagagga aaataaatca gagaaagaca     600
atggatagaa ctggtcagag taataaaaag agaagagaag aggttgtcaa tgaaaactat     660
gaattcaaaa tatttcaaga ctggtcaata atcaattact acagtgaagg caagcagagc     720
aggagttaaa ctgtccaaat ggatttaaaa atagcaagaa actgccaacc tctgaagaaa     780
gaagtttatg tagcatggtg ggaaagaaag ccagaataac tgggctgaag taaagacagt     840
atgtgtagaa tactcctgat ggtgtagaaa aagaaaaata atgggctagt ctagaaggca     900
ggaagaactg aaaatgatgt ttttaagata aggcaatttg agcatatttc ttttttcttt     960
ttgaggcaga gtctcaatct gtcacccagg ctggagtgca atggcgcaat ctcggctcac    1020
tgcaacctcc acctcccagt tcaagtgatt ctcttgcctc agcctctgaa gtagctggga    1080
ctacagatgc agaccaccac acccggctta tttttgtatt tttaatagag acagggtttc    1140
gccatgttgg ccaggctgat ctcgaactcc tgacctccag tgatctgccc acctcggctt    1200
cccaaagtgc tgggattaca ggcataagcc actgcgcccg gcccatttga gcatatttct    1260
aagatgagag gacacaatca atagagagaa agatattaat cagactagta gatgtaatac    1320
aaattttcag ggactgagat gaaaagtaca ggtcaaatag cctttaaaac gtcagtcacg    1380
tgcctctttg ttaaaagaga t                                              1401
```

GENES AND MARKERS IN TYPE 2 DIABETES AND OBESITY

RELATED APPLICATIONS

This application claims the benefit of U.S. provisional Application No. 60/798,706, filed on May 9, 2006; U.S. provisional Application No. 60/798,774, filed on May 9, 2006; U.S. provisional Application No. 60/805,522, filed on Jun. 22, 2006; U.S. provisional Application No. 60/819,015 filed on Jul. 7, 2006; U.S. provisional Application No. 60/827,306, filed on Sep. 28, 2006; U.S. provisional Application No. 60/863,438, filed on Oct. 30, 2006 and U.S. provisional Application No. 60/864,681 filed on Nov. 7, 2006. The entire teachings of the above applications are incorporated herein by reference.

BACKGROUND OF THE INVENTION

The term diabetes mellitus (DM) (ICD/10 codes E10-E14) describes several syndromes of abnormal carbohydrate metabolism that are characterized by hyperglycemia. It is associated with a relative or absolute impairment in insulin secretion, along with varying degrees of peripheral resistance to the action of insulin. According to the new etiologic classification of DM, four categories are differentiated: type 1 diabetes (T1D), type 2 diabetes (T2D), other specific types, and gestational diabetes mellitus (American Diabates Association (ADA), 2003). T2D, accounting for 90% of all diabetes mellitus cases worldwide, is characterized by adult onset insulin resistance and a rise in blood sugar concentration.

The causes of T2D are multi-factorial and include both genetic and environmental elements that affect beta cell function and tissue insulin sensitivity (muscle, liver, adipose tissue, pancreas). Although there is considerable debate as to the relative contributions of beta-cell dysfunction and reduced insulin sensitivity to the pathogenesis of diabetes, it is generally agreed that both of these factors play important roles (Scheen A J, 2003). Both impaired insulin secretion and insulin action cause the development of type 2 diabetes. Insulin resistance is an early feature in the pathophysiology of type 2 diabetes.

T2D is a heterogeneous disease resulting from the interaction of environmental factors such as obesity or sedentary lifestyle, with variety of diabetogenic genes (Stumvoll et al 2005). Abnormal glucose homeostasis occurs when either insulin sensitivity or insulin secretion or both are altered (Bajaj M and Defronzo R A, 2003, Weyer C et al, 1999). An early finding in this development is insulin resistance, defined as impaired insulin-mediated glucose clearance in insulin-sensitive tissues (skeletal muscle, liver and adipose tissue) (Warram J H et al, 1990). Elevation of glucose levels triggers β-cells to produce and secrete more insulin, which compensates for the disturbance in glucose homeostasis (Bajaj M and Defronzo R A, 2003). The duration of hyperglycemia-hyperinsulinemia state depends on insulin secretory capacity, mass and apoptosis rate of β-cells (Porte D, Jr. and Kahn S E, 2001). Furthermore, β-cells can loose their insulin secretion capacity because of glucose toxicity or other reasons (Kaiser N et al, 2003). When β-cells fail to compensate for insulin resistance blood glucose concentration increases. Thus, over time subclinical hyperglycemia tends to progress to impaired glucose tolerance (IGT) and further to type 2 diabetes. However, only 20-50% individuals with primary insulin resistance and IGT develop type 2 diabetes in 10 years (Alberti K G, 1998). Therefore, these individuals have almost undetectable β-cell dysfunction early in the course of the disease. On the other hand, lifestyle intervention and/or administration of insulin-sensitizing drugs may alleviate insulin resistance and prevent or even reverse the progression from IGT to type 2 diabetes (Tuomilehto J et al, 2001).

No major single gene explaining the development of T2D has been identified although more than 30 GWS studies have been performed and more than a hundred candidate genes have been evaluated for T2D. The T2D association of only a handful of T2D candidate genes has been replicated in multiple studies. The association of TCF7L2 and PPARG with T2D is widely reproduced (Deeb SS et al, 1998; Hara K et al, 2000; Altshulert D et al, 2000; Mori H et al, 2001, Grant S F et al, 2006, Saxena R et al, 2006), and that of KCNJ11 (Hani E H et al, 1998; Gloyn A L et al, 2001; Gloyn A L et al, 2003), CAPN10 (Tsuchiya T et al, 2006) and PPARGC1A (Barosso I et al, 2006) have now been replicated by multiple groups.

In 2000, there were approximately 171 million people, worldwide, with diabetes. The number of people with diabetes will expectedly more than double over the next 25 years, to reach a total of 366 million by 2030 (WHO/IDF, 2004). The two main contributors to the worldwide increase in prevalence of diabetes are population ageing and urbanization, especially in developing countries, with the consequent increase in the prevalence of obesity (WHO/IDF, 2004). Currently more than 1 billion adults are overweight—and at least 300 million of them are clinically obese. This suggests the role of relatively modem environmental or behavioral risk factors such as high caloric intake or sedentary lifestyle. However, ethnic differences in the incidence and prevalence of T2D and the enrichment of T2D in families suggest heritable risk factors to play a major role. In the USA, there are over 15 million diabetics and 15 million people with impaired glucose tolerance. Almost one million Americans become diabetic annually.

The chronic hyperglycemia of diabetes is associated with long-term damage, dysfunction, and failure of various organs, especially the eyes, kidneys, nerves, heart, and blood vessels (ADA, 2003). In 2000, 3.2 million people died from complications associated with diabetes. Diabetes has become one of the major causes of premature illness and death in most countries, mainly through the increased risk of cardiovascular disease (CVD). Diabetes is a leading cause of blindness, amputation and kidney failure. These complications account for much of the social and financial burden of diabetes (WHO/IDF, 2004).

Because of the chronic nature of T2D, the severity of its complications and the means required to control them, diabetes is a costly disease, not only for the affected individual and his/her family, but also for the health authorities. In the US direct medical and indirect expenditures attributable to diabetes in 2002 were estimated at $132 billion. Direct medical expenditures alone totalled $91.8 billion and comprised $23.2 billion for diabetes care, $24.6 billion for chronic complications attributable to diabetes, and $44.1 billion for excess prevalence of general medical conditions. Attributable indirect expenditures resulting from lost workdays, restricted activity days, mortality, and permanent disability due to diabetes totalled $39.8 billion (ADA, 2003).

Obesity is an excessive accumulation of energy in the form of body fat which impairs health. As the direct measurement of body fat is difficult, Body Mass Index (BMI), a simple ratio of weight to the square of height ($kg/m^2$), is typically used to classify overweight and obese adults. Consistent with this, the WHO has published international standards for classifying overweight and obesity in adults. There are several causes of obesity as obesity is a complex, multi-factorial chronic disease involving environmental (social and cultural), genetic, physiologic, metabolic, behavioral and psychological components. For example nearly 200 cases of obesity associated with a single gene mutation has been reported (Mutch and Clement, 2006). Twin studies have suggested a heritability of fat mass of between 40% and 70% with a concordance of 0.7-0.9 between monozygotic twins compared to 0.35-0.45 between dizygotic twins (Stunkard et al. 1986)

Although obesity is not a recent phenomenon as the historical roots of obesity can be traced back to 25,000 years ago, the epidemic of obesity is a global health issue across all age groups, especially in industrialized countries (American Obesity Association, 2006). According to WHO's estimate there are more than 300 million obese people (BMI>30) world-wide. Today, for example almost 65% of adult Americans (about 127 million) are categorized as being overweight or obese. There is also evidence that obesity is increasing problem among children, for example in the USA, the percentage of overweight children (aged 5-14 years) has doubled in the last 30 years, from 15% to 32%. The degree of health impairment of obesity is determined by three factors: 1) the amount of fat 2) the distribution of fat and 3) the presence of other risk factors. It is the second leading cause of preventable death in the U.S. Obesity affects all major bodily systems—heart, lung, muscle and bones—and is considered as a major risk factor for several chronic disease conditions, including coronary heart disease (CHD), type 2 diabetes mellitus (T2D), hypertension, stroke, and cancers of the breast, endometrium, prostate and colon (Burton & Foster 1985).

The economic cost attributable to obesity is substantial and is close to $100 billion/yr (Wolf & Colditz 1998). Obesity accounts for 2-6% of total health care costs in several developed countries; some estimates put the figure as high as 7%. The true costs are undoubtedly much greater as not all obesity-related conditions are included in the calculations.

The high prevalence of type 2 diabetes and T2D related conditions such as obesity and increasing population affected shows unmet medical need both for diagnostic methods to identify subjects having increased risk for T2D or a T2D related condition and for better therapies to prevent and to treat T2D and various T2D related conditions. The present invention provides a number of new correlations between various polymorphic alleles and T2D and/or obesity. The T2D and/or obesity associated polymorphic alleles, genes and loci disclosed in this invention provide the basis for improved risk assessment, diagnosis and prognosis of T2D or a T2D related condition, and for the development of novel therapies to prevent and treat T2D or a T2D related condition.

SUMMARY OF THE INVENTION

The present invention relates to previously unknown disease associations between various genes, loci and biomarkers and type 2 diabetes and/or obesity. The detection of these biomarkers provides novel methods and systems for risk assessment, diagnosis or prognosis of T2D or a T2D related condition. In addition the biomarkers provide methods and systems for identifying novel agents for preventing, treating and/or reducing risk of T2D or a T2D related condition. The T2D and/or obesity associated genes can be used to develop novel therapies for prevention and/or treatment of T2D or a T2D related condition such as obesity and the metabolic syndrome.

Accordingly in a first aspect, the present invention provides methods and kits for diagnosing a susceptibility to T2D or a T2D related condition in an individual. The methods comprise the steps of: (i) obtaining a biological sample from the individual, and (ii) detecting in the biological sample one or more T2D and/or obesity associated biomarkers, wherein the biomarkers are related either to one or more genes set forth in tables 1 and 2, and/or are selected from the SNP markers listed in tables 3 to 43. The presence of T2D and/or obesity associated biomarkers is indicative of a susceptibility to type 2 diabetes or a T2D condition. The kits provided for diagnosing a susceptibility to T2D or a T2D related condition in an individual comprise wholly or in part protocol and reagents for detecting one or more biomarkers and interpretation software for data analysis and risk assessment.

In one typical embodiment, the biomarker information obtained from the methods diagnosing a susceptibility of an individual to T2D or a T2D related condition are combined with other information concerning the individual, e.g. results from blood measurements, clinical examination and questionnaires. The blood measurements include but are not restricted to the determination of plasma or serum cholesterol and high-density lipoprotein cholesterol. The information to be collected by questionnaire includes information concerning gender, age, family and medical history such as the family history of obesity and diabetes. Clinical information collected by examination includes e.g. information concerning height, weight, hip and waist circumference and other measures of adiposity and obesity.

In one embodiment, the methods and kits of the invention are used in early diagnosis of T2D or a T2D related condition at or before disease onset, thus reducing or minimizing the debilitating effects of T2D. In a preferred embodiment the methods and kits are applied in individuals who are free of clinical symptoms and signs of T2D or a T2D related condition, but have family history of T2D or obesity or in those who have multiple risk factors of T2D or obesity.

In a second aspect, the present invention provides methods and kits for molecular diagnosis i.e. determining a molecular subtype of T2D or a T2D related condition in an individual. In one preferred embodiment, molecular subtype of T2D in an individual is determined to provide information of the molecular etiology of T2D. When the molecular etiology is known, better diagnosis and prognosis of T2D can be made and efficient and safe therapy for treating T2D in an individual can be selected on the basis of this T2D subtype. For example, the drug that is likely to be effective, i.e. blood glucose lowering, can be selected without trial and error. In other embodiment, biomarker information obtained from methods and kits for determining molecular subtype of T2D in an individual is for monitoring the effectiveness of their treatment. In one embodiment, methods and kits for determining molecular subtype of T2D are used to select human subjects for clinical trials testing antidiabetic drugs. The kits provided for diagnosing a molecular subtype of T2D in an individual comprise wholly or in part protocol and reagents for detecting one or more biomarkers and interpretation software for data analysis and T2D molecular subtype assessment.

In a third aspect, the present invention relates to methods and kits for identifying agents that modulate metabolic activity of a T2D and/or obesity risk gene set forth in tables 1 and 2. Such screening methods and kits are useful when developing drugs having effect on a T2D and/or obesity risk gene of tables 1 and 2, or a related metabolic pathway thereof. The methods and kits comprise contacting a potential modulator with cells expressing one or more T2D and/or obesity risk genes disclosed in tables 1 and 2 and measuring the effect of the potential modulator on activity or function of one or more T2D risk genes or their encoded polypeptides, or on related metabolic pathways. Useful measurements include, but are not limited to expression and mRNA structure of a T2D and/or obesity risk gene, concentration, structure, substrate specificity and biological activity of a T2D and/or obesity risk gene encoded polypeptide, degradation rate of a T2D and/or obesity risk gene encoded polypeptide or mRNA, and biological activity of a T2D and/or obesity risk gene related metabolic pathway. Potential modulators include, but are not limited to, binding partners, agonists, antagonists and antibodies of a T2D and/or obesity risk gene encoded polypeptides.

In a fourth aspect, the present invention relates to novel therapies, pharmaceutical compositions and kits for preventing and/or treating T2D or a T2D related condition in an individual comprising administering, in a pharmaceutical composition, an agent, an recombinant protein or a nucleic acid modulating metabolic activity of a T2D and/or obesity risk gene set forth in tables 1 and 2. In a preferred embodiment, these compositions, methods or kits are used in an individual having T2D or a susceptibility to T2D to compensate altered expression of a T2D risk gene, altered biological activity of T2D risk gene encoded polypeptides or altered function of a T2D risk gene related metabolic pathway when compared to healthy individuals of the same species. Yet in another preferred embodiment therapeutic agent for therapy and/or prevention of T2D or a T2D related condition is selected from the therapeutic agents set forth in table 45 of this invention.

DETAILED DESCRIPTION OF THE INVENTION

The present invention relates to previously unknown associations between T2D and/or obesity and various genes, loci and polymorphisms. These T2D and/or obesity associated genes, loci and polymorphisms provide basis for novel methods and kits for risk assessment, diagnosis and prognosis of T2D or a T2D related condition. In addition these genes, loci and markers provide basis for methods and kits for novel therapies to prevent, treat and/or reduce risk of T2D or a T2D related condition in an individual.

A "biomarker" in the context of the present invention refers to a SNP marker disclosed in tables 3 to 43 or to a polymorphism of a gene disclosed in tables 1 and 2 or at a locus closely linked thereto, or to an organic biomolecule which is related to a gene set forth in tables 1 and 2 and which is differentially present in samples taken from subjects (patients) having type 2 diabetes and/or obesity compared to comparable samples taken from subjects who do not have T2D and/or obesity. An "organic biomolecule" refers to an organic molecule of biological origin, e.g., steroids, amino acids, nucleotides, sugars, polypeptides, polynucleotides, complex carbohydrates or lipids. A biomarker is differentially present between two samples if the amount, structure, function or biological activity of the biomarker in one sample differs in a statistically significant way from the amount, structure, function or biological activity of the biomarker in the other sample.

A "haplotype," as described herein, refers to any combination of genetic markers ("alleles"). A haplotype can comprise two or more alleles and the length of a genome region comprising a haplotype may vary from few hundred bases up to hundreds of kilobases. As it is recognized by those skilled in the art the same haplotype can be described differently by determining the haplotype defining alleles from different nucleic acid strands. E.g. the haplotype GGC defined by the SNP markers rs3936203, rs10933514 and rs4630763 of this invention is the same as haplotype rs3936203, rs10933514, and rs4630763 (CCG) in which the alleles are determined from the other strand, or haplotype rs3936203, rs10933514, and rs4630763 (CGC), in which the first allele is determined from the other strand. The haplotypes described herein are differentially present in individuals with T2D and/or obesity than in individuals without T2D and/or obesity. Therefore, these haplotypes have diagnostic value for risk assessment, diagnosis and prognosis of T2D or a T2D related condition in an individual. Detection of haplotypes can be accomplished by methods known in the art used for detecting nucleotides at polymorphic sites.

The haplotypes described herein, e.g. having markers such as those shown in tables 5, 9, 22, 23, and 31 are found more frequently in individuals with T2D than in individuals without T2D. Therefore, these haplotypes have predictive value for detecting T2D or a susceptibility to T2D in an individual. Some of the haplotypes shown in tables 5, 9, 22, 23, and 31 are found less frequently in individuals with T2D than in individuals without T2D thus reducing the risk of T2D. Similarly, the haplotypes described herein, e.g. having markers such as those shown in tables 36, 39, and 42 are found more frequently in individuals with obesity than in individuals without obesity. Therefore, these haplotypes have predictive value for detecting obesity or a susceptibility to obesity in an individual. Some of the haplotypes shown in tables 36, 39, and 42 are found less frequently in individuals with obesity than in individuals without obesity thus reducing the risk of obesity.

A nucleotide position in genome at which more than one sequence is possible in a population, is referred to herein as a "polymorphic site" or "polymorphism". Where a polymorphic site is a single nucleotide in length, the site is referred to as a SNP. For example, if at a particular chromosomal location, one member of a population has an adenine and another member of the population has a thymine at the same position, then this position is a polymorphic site, and, more specifically, the polymorphic site is a SNP. Polymorphic sites may be several nucleotides in length due to insertions, deletions, conversions or translocations. Each version of the sequence with respect to the polymorphic site is referred to herein as an "allele" of the polymorphic site. Thus, in the previous example, the SNP allows for both an adenine allele and a thymine allele. Typically, a reference nucleotide sequence is referred to for a particular gene e.g. in NCBI databases (www.ncbi.nlm.nih.gov). Alleles that differ from the reference are referred to as "variant" alleles. The polypeptide encoded by the reference nucleotide sequence is the "reference" polypeptide with a particular reference amino acid sequence, and polypeptides encoded by variant alleles are referred to as "variant" polypeptides with variant amino acid sequences. Nucleotide sequence variants can result in changes affecting properties of a polypeptide. These sequence differences, when compared to a reference nucleotide sequence, include insertions, deletions, conversions and substitutions: e.g. an insertion, a deletion or a conversion may result in a frame shift generating an altered polypeptide; a substitution of at least one nucleotide may result in a premature stop codon, amino acid change or abnormal mRNA splicing; the deletion of several nucleotides, resulting in a deletion of one or more amino acids encoded by the nucleotides; the insertion of several nucleotides, such as by unequal recombination or gene conversion, resulting in an interruption of the coding sequence of a reading frame; duplication of all or a part of a sequence; transposition; or a rearrangement of a nucleotide sequence, as described in detail above. Such sequence changes alter the polypeptide encoded by a T2D and/or an obesity susceptibility gene. For example, a nucleotide change resulting in a change in polypeptide sequence can alter the physiological properties of a polypeptide dramatically by resulting in altered activity, distribution and stability or otherwise affect on properties of a polypeptide. Alternatively, nucleotide sequence variants can result in changes affecting transcription of a gene or translation of its mRNA. A polymorphic site located in a regulatory region of a gene may result in altered transcription of a gene e.g. due to altered tissue specificity, altered transcription rate or altered response to transcription factors. A polymorphic site located in a region corresponding to the mRNA of a gene may result in altered translation of the mRNA e.g. by inducing stable secondary structures to the mRNA and affecting the stability of the mRNA. Such sequence changes may alter the expression of a T2D and/or an obesity susceptibility gene.

The SNP markers to which we have disclosed novel T2D and/or obesity associations in tables 3 to 43 of this invention have been known in prior art with their official reference SNP (rs) ID identification tags assigned to each unique SNP by the National Center for Biotechnological Information (NCBI). Each rs ID has been linked to specific variable alleles present in a specific nucleotide position in the human genome, and the nucleotide position has been specified with the nucleotide sequences flanking each SNP. For example the SNP having rs ID rs1535435 is SNP is in chromosome 6 within the AH11 gene, variable alleles are A and G, and the nucleotide sequence assigned to rs 1535435 is (R denotes the variable base):

```
                                              (SEQ ID NO: 1)
GCAATGGGTA AAGTCTTTTA AAAAATTAAG GCATTATGAA

AGATAGTTAT GGAAAGATAA TTTTAGCACA GCAGAGACAG

AGGACTTAGA GACTGAACAC TGAGGTCAAT AGCAACAATT

TAAGCAAAGA GTAATAGGGC TTGAATTAAA GCAAACGCAA

TAGAGAGGAC GTGACAAAAC TGTGAGCCTT TTAGGAGGGA

GAATTGGCAG ACTTTAGTGC TAGTT R GATGTGAAAG

AAATGATGGG AAAGAAAGAA GAGATGAACA CCACTCTGAG

TTTTCAGCTT GGGAGATGGT GGATAAGGAT GCCATTAAAA

TATATGTAAG AGAATTAAAA GAGGAAAACA AAATTTAAGG

AGGTGGGTAA GTTTGGTTTT GGATTTGAGG TGGCAATGGG

CCATTCAAAT GGAAACGTGT AATAGGAAGT CAAATTCATA

AAAAAGGTGT GCGCTAGAAG TCATTAGCAT ATCAGCAAGA

GTCAAAGCTG GGAAAGGTAA GAGAAACTAG GATAAGCATA

TAAAACCAGG AGATGATCAG CTAAAGGATC CTGGGGATAA

AACATATAGA CGATCGGCAG AGGAAAATAA ATCAGAGAAA

GACAATGGAT AGAACTGGTC AGAGTAATAA AAAGAGAAGA

GAAGAGGTTG TCAATGAAAA CTATGAATTC AAAATATTTC

AAGACTGGTC AATAATCAAT TACTACAGTG AAGGCAAGCA

GAGCAGGAGT TAAACTGTCC AAATGGATTT AAAAATAGCA

AGAAACTGCC AACCTCTGAA GAAAGAAGTT TATGTAGCAT

GGTGGGAAAG AAAGCCAGAA TAACTGGGCT GAAGTAAAGA

CAGTATGTGT AGAATACTCC TGATGGTGTA GAAAAGAAA

AATAATGGGC TAGTCTAGAA GGCAGGAAGA ACTGAAAATG

ATGTTTTTAA GATAAGGCAA TTTGAGCATA TTTCTTTTTT

CTTTTTGAGG CAGAGTCTCA ATCTGTCACC CAGGCTGGAG

TGCAATGGCG CAATCTCGGC TCACTGCAAC CTCCACCTCC

CAGTTCAAGT GATTCTCTTG CCTCAGCCTC TGAAGTAGCT

GGGACTACAG ATGCAGACCA CCACACCCGG CTTATTTTTG

TATTTTTAAT AGAGACAGGG TTTCGCCATG TTGGCCAGGC

TGATCTCGAA CTCCTGACCT CCAGTGATCT GCCCACCTCG

GCTTCCCAAA GTGCTGGGAT TACAGGCATA AGCCACTGCG

CCCGGCCCAT TTGAGCATAT TTCTAAGATG AGAGGACACA

ATCAATAGAG AGAAAGATAT TAATCAGACT AGTAGATGTA

ATACAAATTT TCAGGGACTG AGATGAAAAG TACAGGTCAA

ATAGCCTTTA AAACGTCAGT CACGTGCCTC TTTGTTAAAA GAGAT
```

Although the numerical chromosomal position of a SNP may still change upon annotating the current human genome build the SNP identification information such as variable alleles and flanking nucleotide sequences assigned to a SNP will remain the same. Those skilled in the art will readily recognize that the analysis of the nucleotides present in one or more SNPs set forth in tables 3 to 43 of this invention in an individual's nucleic acid can be done by any method or technique capable of determining nucleotides present in a polymorphic site using the sequence information assigned in prior art to the rs IDs of the SNPs listed in tables 3 to 43 of this invention As it is obvious in the art the nucleotides present in polymorphisms can be determined from either nucleic acid strand or from both strands.

It is understood that the T2D and/or obesity associated SNP markers and haplotypes described in tables 3 to 43 of this invention may be associated with other polymorphisms present in same T2D and/or obesity associated genes and loci of this invention. This is because the SNP markers listed in tables 3 to 43 are so called tagging SNPs (tagSNPs). TagSNPs are loci that can serve as proxies for many other SNPs. The use of tagSNPs greatly improves the power of association studies as only a subset of loci needs to be genotyped while maintaining the same information and power as if one had genotyped a larger number of SNPs. These other polymorphic sites associated with the SNP markers listed in tables 3 to 43 of this invention may be either equally useful as biomarkers or even more useful as causative variations explaining the observed T2D and/or obesity association of SNP markers and haplotypes of this invention.

The term "gene," as used herein, refers to an entirety containing entire transcribed region and all regulatory regions of a gene. The transcribed region of a gene including all exon and intron sequences of a gene including alternatively spliced exons and introns so the transcribed region of a gene contains in addition to polypeptide encoding region of a gene also regulatory and 5' and 3' untranslated regions present in transcribed RNA. Each gene of the T2D and/or obesity associated genes disclosed in tables 1 and 2 of this invention has been assigned a specific and unique nucleotide sequence by the scientific community. By using the name of a T2D and/or obesity associated gene provided in tables 1and 2 those skilled in the art will readily find the nucleotide sequences of a gene and it's encoded mRNAs as well as amino acid sequences of it's encoded polypeptides although some genes may have been known with other name(s) in the art.

In certain methods described herein, an individual who is at risk for T2D or a T2D related condition is an individual in whom one or more T2D and/or obesity associated polymorphisms selected from the tables 3 to 43 of this invention are identified. In other embodiment also polymorphisms associated to SNPs and haplotypes of the tables 3 to 43 may be used in risk assessment of T2D or a T2D related condition. The significance associated with an allele or a haplotype is measured by an odds ratio. In a further embodiment, the significance is measured by a percentage. In one embodiment, a significant risk is measured as odds ratio of 0.8 or less or at least about 1.2, including by not limited to: 0.1, 0.2, 0.3, 0.4, 0.5, 0.6, 0.7, 0.8, 1.2, 1.3, 1.4, 1.5, 1.6, 1.7, 1.8, 1.9, 2.0, 2.5, 3.0, 4.0, 5.0, 10.0, 15.0, 20.0, 25.0, 30.0 and 40.0. In a further embodiment, a significant increase or reduction in risk is at least about 20%, including but not limited to about 25%, 30%, 35%, 40%, 45%, 50%, 55%, 60%, 65%, 70%, 75%, 80%, 85%, 90%, 95% and 98%. In a further embodiment, a significant increase in risk is at least about 50%. It is understood however, that identifying whether a risk is medically significant may also depend on a variety of factors such as family history of T2D or obesity, history of gestational diabetes, previously identified glucose intolerance, obesity, hypertriglyceridemia, hypercholesterolemia, elevated LDL cholesterol, low HDL cholesterol, elevated BP, cigarette smoking, lack of physical activity, and inflammatory components as reflected by increased C-reactive protein levels or other inflammatory markers.

"Probes" or "primers" are oligonucleotides that hybridize in a base-specific manner to a complementary strand of nucleic acid molecules. By "base specific manner" is meant that the two sequences must have a degree of nucleotide complementarity sufficient for the primer or probe to hybridize to its specific target. Accordingly, the primer or probe sequence is not required to be perfectly complementary to the sequence of the template. Non-complementary bases or modified bases can be interspersed into the primer or probe, provided that base substitutions do not inhibit hybridization. The nucleic acid template may also include "non-specific priming sequences" or "nonspecific sequences" to which the primer or probe has varying degrees of complementarity. Probes and primers may include modified bases as in polypeptide nucleic acids (Nielsen PE et al, 1991). Probes or primers typically comprise about 15, to 30 consecutive nucleotides present e.g. in human genome and they may further comprise a detectable label, e.g., radioisotope, fluorescent compound, enzyme, or enzyme co-factor. Probes and primers to a SNP marker disclosed in tables 3 to 43 are available in the art or can easily be designed using the flanking nucleotide sequences assigned to a SNP rs ID and standard probe and primer design tools. Primers and probes for SNP markers disclosed in tables 3 to 43 can be used in risk assessment as well as molecular diagnostic methods and kits of this invention.

The invention comprises polyclonal and monoclonal antibodies that bind to a polypeptide encoded by a T2D and/or obesity associated gene set forth in tables 1 and 2 of the invention. The term "antibody" as used herein refers to immunoglobulin molecules or their immunologically active portions that specifically bind to an epitope (antigen, antigenic determinant) present in a polypeptide or a fragment thereof, but does not substantially bind other molecules in a sample, e.g., a biological sample, which contains the polypeptide. Examples of immunologically active portions of immunoglobulin molecules include F(ab) and F(ab').sub.2 fragments which can be generated by treating the antibody with an enzyme such as pepsin. The term "monoclonal antibody" as used herein refers to a population of antibody molecules that are directed against a specific epitope and are produced either by a single clone of B cells or a single hybridoma cell line.

Polyclonal and monoclonal antibodies can be prepared by various methods known in the art. Additionally, recombinant antibodies, such as chimeric and humanized monoclonal antibodies, comprising both human and non-human portions, can be produced by recombinant DNA techniques known in the art. Antibodies can be coupled to various enzymes, prosthetic groups, fluorescent materials, luminescent materials, bioluminescent materials, or radioactive materials to enhance detection.

"A T2D related condition" in the context of this invention refers to glucose intolerance, insulin resistance, metabolic syndrome, obesity, a microvascular complication of T2D such as retinopathy, nephropathy or neuropathy, or a macrovascular complication such as coronary heart disease, cerebrovascular disease, congestive heart failure, claudication or other clinical manifestation of atherosclerosis or arteriosclerosis.

An antibody specific for a polypeptide encoded by a T2D and/or obesity associated gene set forth in tables 1 and 2 of the invention can be used to detect the polypeptide in a biological sample in order to evaluate the abundance and pattern of expression of the polypeptide. Antibodies can be used diagnostically to monitor protein levels in tissue such as blood as part of a test predicting the susceptibility to T2D or a T2D related condition or as part of a clinical testing procedure, e.g., to, for example, determine the efficacy of a given treatment regimen. Highly purified antibodies (e.g. monoclonal humanized antibodies specific to a polypeptide encoded by a T2D and/or obesity associated gene of this invention) may be produced using GMP-compliant manufacturing processes known in the art. These "pharmaceutical grade" antibodies can be used in novel therapies modulating activity and/or function of a polypeptide encoded by a T2D and/or obesity associated gene disclosed in tables 1 and 2 of this invention to treat T2D or a T2D related condition.

Diagnostic Methods and Test Kits

One major application of the current invention is diagnosing a susceptibility to T2D or a T2D related condition. The risk assessment methods and test kits of this invention can be applied to any healthy person as a screening or predisposition test, although the methods and test kits are preferably applied to high-risk individuals (who have e.g. family history of T2D, history of gestational diabetes, previous glucose intolerance, obesity or any combination of these). Diagnostic tests that define genetic factors contributing to T2D might be used together with or independent of the known clinical risk factors to define an individual's risk relative to the general population. Better means for identifying those individuals susceptible for T2D or a T2D related condition should lead to better preventive and treatment regimens, including more aggressive management of the risk factors for T2D or a T2D related condition such as obesity, lack of physical activity, hypercholesterolemia, elevated LDL cholesterol, low HDL cholesterol, elevated BP, cigarette smoking and inflammatory components as reflected by increased C-reactive protein levels or other inflammatory markers. Physicians may use the information on genetic risk factors to convince particular patients to adjust their life style e.g. to stop smoking, to reduce caloric intake or to increase exercise.

In one embodiment of the invention, diagnosis of a susceptibility to T2D or a T2D related condition in a subject, is made by detecting one or more SNP markers and haplotypes disclosed in tables 3 to 43 of this invention in the subject's nucleic acid. The presence of T2D and/or obesity associated alleles of the assessed SNP markers and haplotypes in individual's genome indicates subject's increased risk for T2D or a T2D related condition. The invention also pertains to methods of diagnosing a susceptibility to T2D or a T2D related condition in an individual comprising detection of a haplotype in a T2D and/or obesity risk gene that is more frequently present in an individual having T2D or a T2D related condition (affected), compared to the frequency of its presence in a healthy individual (control), wherein the presence of the haplotype is indicative of a susceptibility to T2D or a T2D related condition. A haplotype may be associated with a reduced rather than increased risk of T2D and/or obesity, wherein the presence of the haplotype is indicative of a reduced risk of T2D or a T2D related condition. In other embodiment of the invention, diagnosis of susceptibility to T2D or a T2D related condition, is done by detecting in the subject's nucleic acid one or more polymorphic sites which are in linkage disequilibrium with one or more SNP markers and haplotypes disclosed in tables 3 to 43 of this invention. Diagnostically the most useful polymorphic sites are those altering the biological activity of a polypeptide encoded by a T2D and/or obesity associated gene set forth in tables 1 and 2. Examples of such functional polymorphisms include, but are not limited to frame shifts; premature stop codons, amino acid changing polymorphisms and polymorphisms inducing abnormal mRNA splicing. Nucleotide changes resulting in a change in polypeptide sequence in many cases alter the physiological properties of a polypeptide by resulting in altered activity, distribution and stability or otherwise affect on properties of a polypeptide. Other diagnostically useful polymorphic sites are those affecting transcription of a T2D and/or obesity associated gene set forth in tables 1 and 2, or translation of it's mRNA due to altered tissue specificity, due to altered transcription rate, due to altered response to physiological status, due to altered translation efficiency of the mRNA and due to altered stability of the mRNA. The presence of nucleotide sequence variants altering the polypeptide structure and/or expression in T2D and/or obesity associated genes of this invention in individual's nucleic acid is diagnostic for susceptibility to T2D.

In diagnostic assays determination of the nucleotides present in one or more T2D and/or obesity associated SNP markers of this invention, as well as polymorphic sites associated with T2D associated SNP markers of this invention, in an individual's nucleic acid can be done by any method or technique which can accurately determine nucleotides present in a polymorphic site. Numerous suitable methods have been described in the art (see e.g. Kwok P-Y, 2001; Syvanen A-C, 2001), these methods include, but are not limited to, hybridization assays, ligation assays, primer extension assays, enzymatic cleavage assays, chemical cleavage assays and any combinations of these assays. The assays may or may not include PCR, solid phase step, a microarray, modified oligonucleotides, labeled probes or labeled nucleotides and the assay may be multiplex or singleplex. As it is obvious in the art the nucleotides present in a polymorphic site can be determined from either nucleic acid strand or from both strands.

In another embodiment of the invention, a susceptibility to T2D or a T2D related condition is assessed from transcription products of one or more T2D and/or obesity associated genes. Qualitative or quantitative alterations in transcription products can be assessed by a variety of methods described in the art, including e.g. hybridization methods, enzymatic cleavage assays, RT-PCR assays and microarrays. A test sample from an individual is collected and the alterations in the transcription of T2D associated genes are assessed from the RNA molecules present in the sample. Altered transcription is diagnostic for a susceptibility to T2D or a T2D related condition.

In another embodiment of the invention, diagnosis of a susceptibility to T2D is made by examining expression, abundance, biological activities, structures and/or functions of polypeptides encoded by one or more T2D and/or obesity related genes disclosed in tables 1 and 2. A test sample from an individual is assessed for the presence of alterations in the expression, biological activities, structures and/or functions of the polypeptides, or for the presence of a particular polypeptide variant (e.g., an isoform) encoded by a T2D and/or obesity risk gene. An alteration can be, for example, quantitative (an alteration in the quantity of the expressed polypeptide, i.e., the amount of polypeptide produced) or qualitative (an alteration in the structure and/or function of a polypeptide encoded by a T2D and/or obesity risk gene, i.e. expression of a mutant polypeptide or of a different splicing variant or isoform). Alterations in expression, abundance, biological activity, structure and/or function of a T2D and/or susceptibility polypeptide can be determined by various methods known in the art e.g. by assays based on chromatography, spectroscopy, colorimetry, electrophoresis, isoelectric focusing, specific cleavage, immunologic techniques and measurement of biological activity as well as combinations of different assays. An "alteration" in the polypeptide expression or composition, as used herein, refers to an alteration in expression or composition in a test sample, as compared with the expression or composition in a control sample and an alteration can be assessed either directly from the T2D and/or obesity susceptibility polypeptide itself or it's fragment or from substrates and reaction products of said polypeptide. A control sample is a sample that corresponds to the test sample (e.g., is from the same type of cells), and is from an individual who is not affected by T2D. An alteration in the expression, abundance, biological activity, function or composition of a polypeptide encoded by a T2D and/or obesity susceptibility gene of the invention in the test sample, as compared with the control sample, is indicative of a susceptibility to T2D. In another embodiment, assessment of the splicing variant or isoform(s) of a polypeptide encoded by a polymorphic or mutant T2D and/or obesity risk gene can be performed directly (e.g., by examining the polypeptide itself), or indirectly (e.g., by examining the mRNA encoding the polypeptide, such as through mRNA profiling).

Yet in another embodiment, a susceptibility to T2D or a T2D related condition can be diagnosed by assessing the status and/or function of biological networks and/or metabolic pathways related to one or more polypeptides encoded by T2D and/or obesity risk genes of this invention. Status and/or function of a biological network and/or a metabolic pathway can be assessed e.g. by measuring amount or composition of one or several polypeptides or metabolites belonging to the biological network and/or to the metabolic pathway from a biological sample taken from a subject. Risk to develop T2D or a T2D related condition is evaluated by comparing observed status and/or function of biological networks and or metabolic pathways of a subject to the status and/or function of biological networks and or metabolic pathways of healthy controls.

Another major application of the current invention is diagnosis of a molecular subtype of T2D or a T2D related condition in a subject. Molecular diagnosis methods and kits of this invention can be applied to a person having T2D or a T2D related condition, although the methods and test kits are preferably applied to persons having familial diabetes (who have family members with T2D). In one preferred embodiment, molecular subtype of T2D in an individual is determined to provide information of the molecular etiology of T2D. When the molecular etiology is known, better diagnosis and prognosis of T2D can be made and efficient and safe therapy for treating T2D in an individual can be selected on the basis of this T2D subtype. For example, the drug that is likely to be effective, i.e. blood glucose lowering, can be selected without trial and error. Physicians may use the information on genetic risk factors with or without known clinical risk factors to convince particular patients to adjust their life style and manage T2D risk factors and select intensified preventive and curative interventions for them. In other embodiment, biomarker information obtained from methods and kits for determining molecular subtype of T2D in an individual is for monitoring the effectiveness of their treatment. In one embodiment, methods and kits for determining molecular subtype of T2D are used to select human subjects for clinical trials testing antidiabetic drugs. The kits provided for diagnosing a molecular subtype of T2D in an individual comprise wholly or in part protocol and reagents for detecting one or more biomarkers and interpretation software for data analysis and T2D molecular subtype assessment.

The diagnostic assays and kits of the invention may further comprise a step of combining non-genetic information with the biomarker data to make risk assessment, diagnosis or prognosis of T2D or a T2D related condition. Useful non-genetic information comprises age, gender, smoking status, physical activity, waist-to-hip circumference ratio (cm/cm), the subject family history of T2D or obesity, history of gestational diabetes, previously identified glucose intolerance, obesity, hypertriglyceridemia, low HDL cholesterol, HT and elevated BP. The detection method of the invention may also further comprise a step determining blood, serum or plasma glucose, total cholesterol, HDL cholesterol, LDL cholesterol, triglyceride, apolipoprotein B and AI, fibrinogen, ferritin, transferrin receptor, C-reactive protein, serum or plasma insulin concentration.

The score that predicts the probability of T2D or a T2D related condition may be calculated e.g. using a multivariate failure time model or a logistic regression equation. The results from the further steps of the method as described above render possible a step of calculating the probability of T2D or a T2D related condition using a logistic regression equation as follows. Probability of T2D or a T2D related condition=$1/[1+e(-(-a+\Sigma(bi*Xi))]$, where e is Napier's constant, Xi are variables related to the T2D or a T2D related condition, bi are coefficients of these variables in the logistic function, and a is the constant term in the logistic function, and wherein a and bi are preferably determined in the population in which the method is to be used, and Xi are preferably selected among the variables that have been measured in the population in which the method is to be used. Preferable values for $b_i$ are between −20 and 20; and for i between 0 (none) and 100,000. A negative coefficient $b_i$ implies that the marker is risk-reducing and a positive that the marker is risk-increasing. Xi are binary variables that can have values or are coded as 0 (zero) or 1 (one) such as SNP markers. The model may additionally include any interaction (product) or terms of any variables Xi, e.g. biXi. An algorithm is developed for combining the information to yield a simple prediction of T2D or a T2D related condition as percentage of risk in one year, two years, five years, 10 years or 20 years. Alternative statistical models are failure-time models such as the Cox's proportional hazards' model, other iterative models and neural networking models.

Diagnostic test kits (e.g. reagent kits) of this invention comprise reagents, materials and protocols for assessing one or more biomarkers, and instructions and software for comparing the biomarker data from a subject to biomarker data from healthy and diseased people to make risk assessment, diagnosis or prognosis of T2D or a T2D related condition. Useful reagents and materials for kits include, but are not limited to PCR primers, hybridization probes and primers as described herein (e.g., labeled probes or primers), allele-specific oligonucleotides, reagents for genotyping SNP markers, reagents for detection of labeled molecules, restriction enzymes (e.g., for RFLP analysis), DNA polymerases, RNA polymerases, DNA ligases, marker enzymes, antibodies which bind to altered or to non-altered (native) T2D and/or obesity risk gene encoded polypeptide, means for amplification of nucleic acids fragments from one or more T2D and/or obesity risk genes selected from the tables 1 and 2, means for analyzing the nucleic acid sequence of one or more T2D and/or obesity risk genes or fragments thereof, or means for analyzing the sequence of one or more amino acid residues of T2D and/or obesity risk gene encoded polypeptides, etc. In one embodiment, a kit for diagnosing susceptibility to T2D or a T2D related condition comprises primers and reagents for detecting the nucleotides present in one or more SNP markers selected from the tables 3 to 43 in individual's nucleic acid.

Yet another application of the current invention is related to methods and test kits for monitoring the effectiveness of a treatment for T2D or a T2D related condition. The disclosed methods and kits comprise taking a tissue sample (e.g. peripheral blood sample or adipose tissue biopsy) from a subject before starting a treatment, taking one or more comparable samples from the same tissue of the subject during the therapy, assessing expression (e.g., relative or absolute expression) of one or more T2D and/or obesity risk genes set forth in tables 1 and 2 in the collected samples of the subject and detecting differences in expression related to the treatment. Differences in expression can be assessed from mRNAs and/or polypeptides encoded by one or more T2D and/or obesity risk genes of the invention and an alteration in the expression towards the expression observed in the same tissue in healthy individuals indicates the treatment is efficient. In a preferred embodiment the differences in expression related to a treatment are detected by assessing biological activities of one or more polypeptides encoded by T2D and/or obesity risk genes set forth in tables 1 and 2.

Alternatively the effectiveness of a treatment for T2D and/or obesity can be followed by assessing the status and/or function of metabolic pathways related to one or more polypeptides encoded by T2D and/or obesity risk genes set forth in tables 1 and 2. Status and/or function of a metabolic pathway can be assessed e.g. by measuring amount or composition of one or morel polypeptides, belonging to the metabolic pathway, from a biological sample taken from a subject before and during a treatment. Alternatively status and/or function of a metabolic pathway can be assessed by measuring one or more metabolites belonging to the metabolic pathway, from a biological sample before and during a treatment. Effectiveness of a treatment is evaluated by comparing observed changes in status and/or function of metabolic pathways following treatment with T2D therapeutic agents to the data available from healthy subjects.

Methods of Therapy

The present invention discloses novel methods for the prevention and treatment of T2D or a related condition. In particular, the invention relates to methods of treatment for T2D or susceptibility to T2D as well as to methods of treatment for manifestations and subtypes of T2D.

The term, "treatment" as used herein, refers not only to ameliorating symptoms associated with the disease, but also preventing or delaying the onset of the disease, and also lessening the severity or frequency of symptoms of the disease, preventing or delaying the occurrence of a second episode of the disease or condition; and/or also lessening the severity or frequency of symptoms of the disease or condition.

The present invention encompasses methods of treatment (prophylactic and/or therapeutic) for T2D or a T2D related condition using a T2D therapeutic agent. A "T2D therapeutic agent" is an agent that alters (e.g., enhances or inhibits) enzymatic activity or function of a T2D and/or obesity risk affecting polypeptide, and/or expression of a T2D and/or obesity risk gene disclosed in tables 1 and 2. Useful therapeutic agents can alter biological activity or function of a T2D and/or obesity susceptibility polypeptide and/or expression of related gene by a variety of means, for example, by altering translation rate of a T2D and/or obesity susceptibility polypeptide encoding mRNA; by altering transcription rate of a T2D and/or obesity risk gene; by altering posttranslational processing rate of a T2D and/or obesity susceptibility polypeptide; by interfering with a T2D and/or obesity susceptibility polypeptide biological activity and/or function (e.g., by binding to a T2D susceptibility polypeptide); by altering stability of a T2D and/or obesity susceptibility polypeptide; by altering the transcription rate of splice variants of a T2D and/or obesity risk gene or by inhibiting or enhancing the elimination of a T2D and/or obesity susceptibility polypeptide from target cells, organs and/or tissues.

Representative therapeutic agents of the invention comprise the following: (a) nucleic acids, fragments, variants or derivatives of the T2D and/or obesity associated genes of this invention, nucleic acids encoding a T2D and/or obesity susceptibility polypeptide or an active fragment or a derivative thereof and nucleic acids modifying the expression of said T2D and/or obesity genes (e.g. antisense polynucleotides, catalytically active polynucleotides (e.g. ribozymes and DNAzymes), molecules inducing RNA interference (RNAi) and micro RNA), and vectors comprising said nucleic acids; (b) T2D susceptibility polypeptides, active fragments, variants or derivatives thereof, binding agents of T2D and/or obesity susceptibility polypeptides; peptidomimetics; fusion proteins or prodrugs thereof, antibodies (e.g., an antibody to a mutant T2D and/or obesity susceptibility polypeptide, or an antibody to a non-mutant T2D and/or obesity susceptibility polypeptide, or an antibody to a particular variant encoded by a T2D and/or obesity risk gene, as described above) and other polypeptides (e.g., T2D and/or obesity susceptibility receptors, active fragments, variants or derivatives thereof); (c) metabolites of T2D and/or obesity susceptibility polypeptides or derivatives thereof; (d) small molecules and compounds that alter (e.g., inhibit or antagonize) a T2D and/or obesity risk gene expression, activity and/or function of a T2D and/or obesity risk gene encoded polypeptide, or activity and/or function of a T2D and/or obesity gene related metabolic pathway and; (e) small molecules and compounds that alter (e.g. induce, agonize or modulate) a T2D and/or obesity risk gene expression, activity and/or function of a T2D and/or obesity risk gene encoded polypeptide, or activity and/or function of a T2D and/or obesity gene related metabolic pathway.

The nucleic acid sequences assigned in the art to the T2D and/or obesity associated genes provided in tables 1 and 2 of this invention are publicly available and can be used to design and develop therapeutic nucleic acid molecules and recombinant DNA molecules for the prevention and treatment of T2D or a T2D related condition. For example antisense nucleic acid molecules targeted to a gene listed in tables 1 and 2 can be designed using tools and the nucleotide sequence of the gene available in the art and constructed using chemical synthesis and/or enzymatic ligation reactions using procedures known in the art. For example, an antisense nucleic acid molecule (e.g., an antisense oligonucleotide) can be chemically synthesized using naturally occurring nucleotides or modified nucleotides designed to increase the biological stability of the molecules or to increase the physical stability of the duplex formed between the antisense oligonucleotide and sense nucleic acids, e.g., phosphorothioate derivatives and acridine substituted nucleotides can be used.

Alternatively, the antisense nucleic acid molecule can be produced biologically using an expression vector into which a nucleic acid molecule encoding a T2D and/or obesity risk gene, a fragment or a variant thereof has been cloned in antisense orientation (i.e., RNA transcribed from the expression vector will be complementary to the transcribed RNA of a T2D and/or obesity risk gene of interest).

More than one T2D therapeutic agent can be used concurrently, if desired. The therapy is designed to alter (e.g., inhibit or enhance), replace or supplement activity and/or function of one or more T2D and/or obesity polypeptides or related metabolic pathways in an individual. For example, a T2D therapeutic agent can be administered in order to upregulate or increase the expression or availability of a T2D and/or obesity risk gene or a specific variant of a T2D and/or obesity susceptibility gene or, conversely, to downregulate or decrease the expression or availability of a T2D and/or obesity risk gene or a specific variant of a T2D and/or obesity risk gene. Upregulation or increasing expression or availability of a native T2D and/or obesity risk gene or a particular variant of a T2D and/or obesity susceptibility gene could interfere with or compensate for the expression or activity of a defective gene or variant; downregulation or decreasing expression or availability of a native T2D risk gene or a particular splicing variant of a T2D susceptibility gene could minimize the expression or activity of a defective gene or the particular variant and thereby minimize the impact of the defective gene or the particular variant.

The T2D therapeutic agent(s) are administered in a therapeutically effective amount (i.e., an amount that is sufficient to treat the disease, such as by ameliorating symptoms associated with the disease, preventing or delaying the onset of the disease, and/or also lessening the severity or frequency of symptoms of the disease). The amount which will be therapeutically effective in the treatment of a particular individual's disorder or condition will depend on the symptoms and severity of the disease, and can be determined by standard clinical techniques. In addition, in vitro or in vivo assays may optionally be employed to help identify optimal dosage ranges. The precise dose to be employed in the formulation will also depend on the route of administration, and the seriousness of the disease or disorder, and should be decided according to the judgment of a practitioner and each patient's circumstances. Effective doses may be extrapolated from dose-response curves derived from in vitro or animal model test systems.

In one embodiment, a nucleic acid encoding a T2D and/or obesity susceptibility polypeptide, fragment, variant or derivative thereof, either by itself or included within a vector, can be introduced into cells of an individual affected by T2D or a T2D related condition using variety of experimental methods described in the art, so that the treated cells start to produce native T2D and/or obesity susceptibility polypeptide. Thus, cells which, in nature, lack of a native T2D and/or obesity risk gene expression and activity, or have abnormal T2D and/or obesity risk gene expression and activity, can be engineered to express a T2D and/or obesity susceptibility polypeptide or an active fragment or a different variant of said T2D and/or obesity susceptibility polypeptide. Genetic engineering of cells may be done either "ex vivo" (i.e. suitable cells are isolated and purified from a patient and re-infused back to the patient after genetic engineering) or "in vivo" (i.e. genetic engineering is done directly to a tissue of a patient using a vehicle). Alternatively, in another embodiment of the invention, a nucleic acid (e.g. a polynucleotide) which specifically hybridizes to the mRNA and/or genomic DNA of a T2D and/or obesity risk gene is administered in a pharmaceutical composition to the target cells or said nucleic acid is generated "in vivo". The antisense nucleic acid that specifically hybridizes to the mRNA and/or DNA inhibits expression of the T2D and/or obesity susceptibility polypeptide, e.g., by inhibiting translation and/or transcription. Binding of the antisense nucleic acid can be due to conventional base pairing, or, for example, in the case of binding to DNA duplexes, through specific interaction in the major groove of the double helix. In a preferred embodiment nucleic acid therapeutic agents of the invention are delivered into cells that express one or more T2D and/or obesity risk genes. A number of methods including, but not limited to, the methods known in the art can be used for delivering a nucleic acid to said cells. For example, a vector can be introduced in vivo such that it is taken up by a cell and directs the transcription of a RNA molecule, which induces RNA interference in the cell. Such a vector can remain episomal or become chromosomally integrated, and as long as it can be transcribed to produce the desired RNA molecules it will modify the expression of a T2D and/or obesity risk gene. Such vectors can be constructed by various recombinant DNA technology methods standard in the art.

The expression of an endogenous T2D and/or obesity risk gene can be reduced by inactivating or "knocking out" a T2D and/or obesity risk gene or its promoter using targeted homologous recombination methods described in the art. Alternatively, expression of a functional, non-mutant T2D and/or obesity risk gene can be increased using a similar method: targeted homologous recombination can be used to replace a non-functional T2D and/or obesity risk gene with a functional form of the said gene in a cell. In yet another embodiment of the invention, other T2D therapeutic agents as described herein can also be used in the treatment or prevention of T2D or a related condition. The therapeutic agents can be delivered in a pharmaceutical composition they can be administered systemically, or can be targeted to a particular tissue. The therapeutic agents can be produced by a variety of means, including chemical synthesis, cell culture and recombinant techniques (e.g. with transgenic cells and animals). Therapeutic agents can be isolated and purified to fulfill pharmaceutical requirements using standard methods described in the art. A combination of any of the above methods of treatment (e.g., administration of non-mutant T2D and/or obesity susceptibility polypeptide in conjunction with RNA molecules inducing RNA interference targeted to the mutant T2D and/or obesity susceptibility mRNA) can also be used.

In the case of pharmaceutical therapy, the invention comprises compounds, which enhance or reduce the activity and/or function of one or several polypeptides encoded by T2D and/or obesity susceptibility genes set forth in tables 1 and 2. The treatment may also enhance or reduce the expression of one or several genes selected from T2D and/or obesity susceptibility genes set forth in tables 1 and 2. In another embodiment of the invention, pharmaceutical therapy of the invention comprises compounds, which enhance or reduce the activity and/or function of one or morel metabolic pathways related to T2D and/or obesity susceptibility genes, proteins or polypeptides. The treatment may also enhance or reduce the expression of one or more genes in metabolic pathways related to T2D and/or obesity susceptibility genes, proteins or polypeptides.

Furthermore, a disclosed method or a test based on T2D and/or obesity susceptibility gene specific biomarkers (e.g. polymorphic sites, expression or polypeptides) is useful in selecting drug therapy for patients with T2D. For example if the less frequent, i.e. the minor, assumable mutated allele in the T2D susceptibility gene is risk-reducing, and if said mutation is a gene function reducing mutation, one can deduce that the gene function and/or activity would increase the risk of T2D. On that basis, drugs and other therapies such as gene therapies that reduce or inhibit the function or activity of the T2D susceptibility gene or the encoded protein would reduce the risk of the said disease and could be used to both prevent and treat the said disease in subjects having said mutated allele.

In another embodiment of the invention a T2D therapeutic agent comprises a know therapeutic agent related to a T2D and/or obesity associated gene listed in tables 1 and 2 of this invention but which is not used to treat T2D or a T2D related condition. Such agents are useful for developing new therapies for T2D or a T2D related condition as they probably are agonizing, modulating, binding, inhibiting and/or antagonizing (i) expression of a T2D and/or obesity risk gene, (ii) biological activity and/or function of a T2D and/or obesity risk gene encoded polypeptide, or (iii) biological activity and/or function of a T2D and/or obesity gene related metabolic pathway. These agents may be used alone or with combination with other treatments and agents used for prevention or treatment of T2D or a T2D related condition.

In a preferred embodiment a T2D therapeutic agent comprises an agent selected from the therapeutic agents disclosed in table 44 of this invention. The fact that the disclosed agents include agents currently used for treating T2D and/or obesity such as different types of insulin, acarbose, and benzphetamine as set forth in table 45 provides support that also the disclosed agents which are not used to treat T2D or a T2D related condition are useful for developing novel therapies for treating T2D or a T2D related condition. This also provides further evidence for the concept that any gene of the present invention set forth in tables 1 and 2 is a potential target for the development of new therapies for the treatment of T2D and/or obesity or a related condition. The person skilful in the art is able to obtain information related to synthesis, mode of action and current indications of each therapeutic agent using the CAS reference number given in tables 44 and 45. All of the therapeutic agents target at least one of the discovered T2D and/or obesity associated genes set forth in Tables 1 and 2.

In another embodiment of the invention the therapeutic compounds presented in table 45 and associated with drug induced diabetes and glucose intolerance may be used to develop new therapies for preventing and treating T2D or a T2D related condition. Examples of such agents are tacrolimus and pimecrolimus which are known calcineurin inhibitors targeting the PPP3CA gene of the current invention. Although these compounds are not applicable for the treatment of T2D and/or obesity or a related condition, they provide further evidence that PPP3CA gene is a true T2D gene and agonist compounds targeting PPP3CA may be beneficial drugs for T2D.

In one embodiment of the invention therapeutic agents or compounds currently known and used for the treatment of T2D and/or obesity are combined with one or more therapeutic agents disclosed in table 44. Known therapeutic agents used to treat T2D and/or obesity comprise insulin secretagogues such as i) sulphonylureas; ii) tolbutamide; iii) chlorpropamide; iv) glimepiride; v) glipizide; vi) glyburide; vii) meglitinides; viii) repaglinide; ix) pramlintide; x) morphilinoguanide; xi) acetylcholine; xii) muscannic agonists; xiii) carbachol; xiv) bethanechol; xv) beta-L-glucose pentaacetate; xvi) chiro-inositol; xvii) myo-inositol; xviii) GIP; xix) GLP-1; and xx) Extendin-4; insulin sensitizers such as i) metformin, ii) rosiglitazone, iii) pioglitazone; insulin such as i)insulin glargine, ii) insulin aspart, iii) insulin lispro, iv) insulin glulisine; v) insulin detemir; glucose reabsobcijos inhibitor such as i) acarbose, ii) miglitol, iii) alpha-glucosidase inhibitor.

There are various mechanisms how the therapeutic agents and compounds set forth in table 44 could be beneficial for subjects suffering from T2D and/or obesity or a related condition. Examples of beneficial mechanisms/pathways for the treatment of T2D and/or obesity or a related condition include, but are not limited to direct or indirect influence on (i) insulin signalling pathway via proteins such as ACCN1, AKT2, PRKCA; (ii) G-coupled receptors such as ADRALA, CASR, GRM1, GRM3, GRM5, GRM7, GRM8, HTR4, HTR7, OPRD1, OPRM1, PTGER2; (iii) ion channels regulating calcium homeostasis such as CACNA1D, CACNA2D1; (iv) ion channels regulating sodium homeostasis such as SCN2A2, SCN5A, SCN3A, SCN3B, SCN8A; (v) ion channels regulating potassium homeostasis such as KCNH2; (vi) other types of ion channels such as GABRA4, GRIA3, GRIN3A, GABRB2, GABRB3, GABRG3; (vii) enzymes such as AKR1B1, ALOX5, CYP19A1, GUCY1A2, MAOB, MGAM, MGMT, PDE11A, PDE4B, POLA1, POLDI, RRM1, TYR, XDH; (viii) ligand-dependent nuclear receptors such as AR, ESR1, NR3C2, PGR, RXRG, THRB.

In one embodiment a T2D therapeutic agent of this invention comprises one or more agents selected from the table 44 and used or being developed for the treatment of neurogenerative diseases such as Alzheimer's disease, Parkinson's disease or dementia. Neurogenerative diseases and metabolic diseases of our invention share common features in their pathophysiology (Ristow M, 2004) including but not limited to: (i) Amyloid accumulation observed both in T2D and Alzheimer's disease. In fact islet amyloid polypeptide which accumulates in pancreatic beta cells secreting insulin share about 90% structural similarity with amyloid A beta precursor protein which accumulates during the development of Alzheimer. Moreover, Parkinson's disease is also a filamentous disorder; (ii) Both Alzheimer's and Parkinson's diseases are associated with increased predisposition to insulin resistance, insulin hypersecretion, T2D and impaired glucose tolerance; and (iii) Glutaminergic and dopaminergic signalling systems are involved in the pathogenesis of Alzheimer's and Parkinson's diseases as well as in insulin secretion, mitochondrial biogenesis and adipogenesis. It is known that treatment with dopamine antagonist induce obesity and T2D (Pij1 H, 2003). Therefore, pharmaceutical compositions comprising a MAOB inhibitor and currently used to treat neurogenerative and psychiatric disorders will be effective in the treatment of T2D and/or obesity and related conditions as they increase amount of available dopamine in cells and tissues.

In another embodiment of the invention a T2D and/or obesity therapeutic agent of this invention comprises one or more agents selected from the table 44 affecting calcium homeostasis. Examples of such agents include but not limited to bepridil, isradipine, nicardipine, nisoldipine, amlodipine and pregabalin. Prevention of calcium overload is beneficial against beta-cell apoptosis and/or necrosis which are enhanced in diabetic state due to gluco-toxicity, lipo-toxicity and increased amount of circulating cytokines such as TNFalpha and IL-1beta. Decrease in skeletal muscle and adipose tissue $[Ca^{2+}]_i$ will alleviate calcium-induced insulin-resistance and improve insulin-stimulated glucose uptake in those tissues. Certainly not to be excluded other actions mediated by calcium release such as function of autonomous and central nervous systems, associated with insulin resistance and obesity via sympathetic nervous system and metabolically active neuropeptides.

In yet another embodiment of the invention a T2D and/or obesity therapeutic agent of this invention comprises one or more agents selected from the table 44 affecting gamma-aminobutyric acid (GABA) A and/or B receptors. Stimulation of these receptors increases insulin content and secretion as well as protects pancreatic beta-cells against apoptosis (Ligon B et al, 2007). Moreover, GABA stimulation decreases glucagon (anti-insulin hormone) secretion from pancreatic alpha cell (Bailey S J et al, 2007).

Still in another embodiment of the invention a T2D and/or obesity therapeutic agent of this invention comprises one or more agents selected from the table 44 targeting PDE1 A, PDE4B and PDE7B. Tolbutamide currently used to treat T2D also targets PDE1 A, PDE4B and PDE7B (Mosby's Drug Consult, 1973). Therefore, other therapeutic agents acting as tolbutamide will be useful for treating T2D and/or obesity or a related condition. Yet in another embodiment of the invention a T2D and/or obesity therapy of this invention comprises a drug combination selected from the table 46. The drug combinations set forth in table 46 are currently used to treat diseases other than T2D or a T2D related condition. However, each said drug combination contains at least one therapeutic agent targeting one or more T2D and/or obesity associated genes disclosed in tables 1 and 2 of this invention so a drug combination selected from the table 46 is useful for prevention and/or treatment of T2D or a T2D related condition.

Pharmaceutical Compositions

The present invention also pertains to pharmaceutical compositions comprising agents described herein, particularly polynucleotides, polypeptides and any fractions, variants or derivatives of T2D and/or obesity susceptibility genes, and/or agents that alter (e.g., enhance or inhibit) expression of a T2D and/or obesity risk gene or genes, or activity of one or more polypeptides encoded by T2D and/or obesity susceptibility genes as described herein. For instance, an agent that alters expression of a T2D and/or obesity risk gene, or activity of one or more polypeptides encoded by T2D susceptibility genes or a T2D and/or obesity susceptibility polypeptide binding agent, binding partner, fragment, fusion protein or prodrug thereof, or polynucleotides of the present invention, can be formulated with a physiologically acceptable carrier or excipient to prepare a pharmaceutical composition. The carrier and composition can be sterile. The formulation should suit the mode of administration. In a preferred embodiment pharmaceutical compositions comprise agent or agents reversing, at least partially, T2D or a T2D related condition associated with changes in metabolic pathways related to the T2D and/or obesity associated genes of this invention.

Agents described herein can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc. Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active agents.

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, polyvinyl pyrolidone, sodium saccharine, cellulose, magnesium carbonate, etc.

Methods of introduction of these compositions include, but are not limited to, intradermal, intramuscular, intraperitoneal, intraocular, intravenous, subcutaneous, topical, oral and intranasal. Other suitable methods of introduction can also include gene therapy (as described below), rechargeable or biodegradable devices, particle acceleration devises ("gene guns") and slow release polymeric devices. The pharmaceutical compositions of this invention can also be administered as part of a combinatorial therapy with other agents. The composition can be formulated in accordance with the routine procedures as a pharmaceutical composition adapted for administration to human beings. For example, compositions for intravenous administration typically are solutions in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration. For topical application, nonsprayable forms, viscous to semi-solid or solid forms comprising a carrier compatible with topical application and having a dynamic viscosity preferably greater than water, can be employed. Suitable formulations include but are not limited to solutions, suspensions, emulsions, creams, ointments, powders, enemas, lotions, sols, liniments, salves, aerosols, etc., which are, if desired, sterilized or mixed with auxiliary agents, e.g., preservatives, stabilizers, wetting agents, buffers or salts for influencing osmotic pressure, etc. The agent may be incorporated into a cosmetic formulation. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., pressurized air.

The agents are administered in a therapeutically effective amount. The amount of agents which will be therapeutically effective in the treatment of a particular disorder or condition will depend on the nature of the disorder or condition, and can be determined by standard clinical techniques. In addition, in vitro or in vivo assays may optionally be employed to help identify optimal dosage ranges. The precise dose to be employed in the formulation will also depend on the route of administration, and the seriousness of the symptoms of T2D or a T2D related condition, and should be decided according to the judgment of a practitioner and each patient's circumstances. Effective doses may be extrapolated from dose-response curves derived from in vitro or animal model test systems.

Functional Foods

By definition "functional foods" or "nutraceuticals" are foods or dietary components or food ingredients that may provide a health benefit beyond basic nutrition. Functional foods are regulated by authorities (e.g. by the FDA in US) according to their intended use and the nature of claims made on the package. Functional foods can be produced by various methods and processes known in the art including, but not limited to synthesis (chemical or microbial), extraction from a biological material, mixing functional ingredient or component to a regular food product, fermentation or using a biotechnological process. A functional food may exert its effects directly in the human body or it may function e.g. through human intestinal bacterial flora.

The T2D and/or obesity associated genes disclosed in tables 1 and 2 of this invention can be used as molecular targets towards which functional foods claiming health benefit in T2D or a T2D related condition can be developed. For example a functional food may compensate reduced biological activity of a polypeptide encoded by a T2D and/or obesity gene set forth in tables 1 and 2 when the T2D and/or obesity risk gene is defective or is not expressed properly in a subject. A functional food may also inhibit the expression and/or biological activity of a gene or polypeptide of the invention promoting the development of T2D or a T2D related condition. In another embodiment a functional food may increase the expression and/or biological activity of a gene or polypeptide protecting an individual from the development of T2D or a T2D related condition due to reduced expression and protein production.

In one embodiment of this invention functional foods for treating T2D or a T2D related condition such as obesity act by reducing increased food intake e.g. by affecting proteins such as neuropeptide Y, NPY receptors, melanin-concentrating hormone, melanocortin receptors, proopiomelanocortin, insulin receptor, corticotropin-releasing hormone, glucocorticoid receptor, interleukin-1 and interleukin-6, human single-minded-1, steroidogenic factor-1, brain-derived neurotrophic factor, dopamine, ghrelin, cholecystokinin or glucagon-like-peptide-1. In other embodiment of this invention functional foods increase energy expenditure by affecting proteins such as the uncoupling proteins, beta-adrenergic receptors or protein kinase A regulatory subunit IIb. Yet in another embodiment of this invention functional foods act through affecting the partitioning of food substrates e.g. by influencing proteins such as CCAAT-enhancer binding proteins, peroxisome-proliferator activated receptor alpha, gamma, cAMP response element binding protein, tumor necrosis factor alpha, high mobility group IC, sterol-regulatory element-binding protein-1c, Acyl CoA:diacylglycerol transferase or hormone-sensitive lipase.

This application includes tables that are submitted in electronic form. The tables are submitted herewith on one original and one duplicate compact disc (in compliance with 37 C.F.R. §1.52(e)) designated respectively as Copy 1 and Copy 2, and labeled in compliance with 37 C.F.R. §1.52(e)(6). All the material in the tables on compact disc is hereby incorporated in their entirety herein by reference, and identified by the following data of file names, creation date and size in bytes:

| FILE NAME | CREATED | SIZE IN BYTES |
| --- | --- | --- |
| Table 1.txt | 3 May 2007 | 60 300 |
| Table 2.txt | 3 May 2007 | 38 100 |
| Table 3.txt | 3 May 2007 | 22 600 |
| Table 4.txt | 3 May 2007 | 24 700 |
| Table 5.txt | 3 May 2007 | 8 090 |
| Table 6.txt | 3 May 2007 | 27 100 |
| Table 7.txt | 3 May 2007 | 39 100 |
| Table 8.txt | 3 May 2007 | 39 400 |
| Table 9.txt | 3 May 2007 | 13 400 |
| Table 10.txt | 3 May 2007 | 30 100 |
| Table 11.txt | 3 May 2007 | 31 100 |
| Table 12.txt | 3 May 2007 | 39 500 |
| Table 13.txt | 3 May 2007 | 27 700 |
| Table 14.txt | 3 May 2007 | 39 600 |
| Table 15.txt | 3 May 2007 | 25 700 |
| Table 16.txt | 3 May 2007 | 39 600 |
| Table 17.txt | 3 May 2007 | 23 200 |
| Table 18.txt | 3 May 2007 | 33 700 |
| Table 19.txt | 3 May 2007 | 29 300 |
| Table 20.txt | 3 May 2007 | 31 500 |
| Table 21.txt | 3 May 2007 | 28 300 |
| Table 22.txt | 3 May 2007 | 21 400 |
| Table 23.txt | 3 May 2007 | 16 800 |
| Table 24.txt | 3 May 2007 | 29 300 |
| Table 25.txt | 3 May 2007 | 24 300 |
| Table 26.txt | 3 May 2007 | 22 200 |
| Table 27.txt | 3 May 2007 | 18 300 |
| Table 28.txt | 3 May 2007 | 19 400 |
| Table 29.txt | 3 May 2007 | 18 400 |
| Table 30.txt | 3 May 2007 | 30 400 |
| Table 31.txt | 3 May 2007 | 35 600 |
| Table 32.txt | 3 May 2007 | 31 200 |
| Table 33.txt | 3 May 2007 | 34 100 |
| Table 34.txt | 3 May 2007 | 26 800 |
| Table 35.txt | 3 May 2007 | 27 100 |
| Table 36.txt | 3 May 2007 | 5 880 |
| Table 37.txt | 3 May 2007 | 25 800 |
| Table 38.txt | 3 May 2007 | 29 500 |
| Table 39.txt | 3 May 2007 | 7 670 |
| Table 40.txt | 3 May 2007 | 26 300 |
| Table 41.txt | 3 May 2007 | 26 300 |
| Table 42.txt | 3 May 2007 | 24 000 |
| Table 44.txt | 3 May 2007 | 181 000 |
| Table 45.txt | 3 May 2007 | 8 140 |
| Table 46.txt | 3 May 2007 | 26 400 |

Tables 43 to 46 are presented in landscape orientation in the above files. The rest of the tables are in portrait orientation.

EXPERIMENTAL SECTION

Example 1

Obesity Study in the KIHD Cohort: The Study Subjects and Genome-Wide Scanning using Affymetrix 100k Assay Obesity associated genes and markers were discovered using the data of the Jurilab's acute myocardial infarction whole genome association study (AMI-GWS). The basics of the AMI-GWS study i.e. the KIHD cohort, the selection of 250 subjects from the KIDH cohort (125 cases and 125 matched controls) and the GWS with the Affymetrix 100 k assays have been described in detail in Jurilab's patent application WO2006/040409. This invention is based on the substudy of the KIHD named "Gen-Epi", which was approved by the national research ethics committee of Finland ("ETENE").

Among the 250 AMI-GWS study subjects there were 59 obesity cases and 83 matched controls. The body-mass index (BMI) was defined as the weight in kilograms divided by the height in meters, squared. The subscapular skinfold thickness was used as a measure of central obesity. The obesity cases were defined as those with BMI of 30 $kg/m^2$ or more and controls those with BMI less than 25 kg/m 2. For analysis of continuous variables, BMI was available for all 250 subjects (mean 26.4, standard deviation 3,65 and range from 18.8 to 46.7) and the subscapular skinfold thickness was available for 246 subjects (mean 14.1, standard deviation 6.18 and range from 5.2 to 56.5). Waist-to-hip ratio (WHR) was calculated as the ratio of waist circumference (average of one measure taken after inspiration and one taken after expiration at the midpoint between the lowest rib and the iliac crest) to hip circumference (measured at the level of the trochanter major).

Example 2

Type 2 Diabetes Study in Eastern Finnish, Ashkenazi Jewish, German and English Subjects: The Study Subjects and Genome Wide Scanning using Illumina's HumanHap300

Eastern Finnish (EF) Study Population

The current population of the North Savo is over 250,000 people. The population is genetically homogenous and has a high prevalence of type 2 diabetes. Mailed health-related surveys show consistently very high participation rates. There is almost no illiteracy. The "North Savo Health Survey" was approved by the local ethics committee and it was carried out in October to December, 2003. The survey was targeted to all households in the municipalities of Kuopio, Karttula, Lapinlahti, Leppävirta, Maaninka, Rautalampi, Siilinjärvi, Suonenjoki, Tervo, Vehmersalmi, and Vesanto. The number of households was about 70,000 and the number of people

LENGTHY TABLES

The patent contains a lengthy table section. A copy of the table is available in electronic form from the USPTO web site (http://seqdata.uspto.gov/?pageRequest=docDetail&DocID=US07901885B2). An electronic copy of the table will also be available from the USPTO upon request and payment of the fee set forth in 37 CFR 1.19(b)(3).

over 18 years old was about 200,000. A letter was sent to each household containing three personal and one common questionnaire. The three oldest persons who were at least 18 years of age in the household were asked to fill in the personal questionnaire and one of them to fill in the common family data questionnaire, and return them in the same single return envelope. Only persons, who gave the consent to obtain their hospital records and who provided their personal identification code, were asked to return the questionnaire. The "North Savo Project" included the collection of disease, family, drug response and contact information. By the end of 2004, 17,100 participants were surveyed. The North Savo Survey data were used to identify probands with T2D.

In the second phase, the "SOHFA" project, patients with T2D and T2D-free controls were examined. SOHFA is a contractual study, in which the University of Kuopio is the contractee. "GEDINO" (Genetics of type 2 diabetes in North Savo) is a similar contractual project, in which the T2D cases and controls were collected by using a newspaper advertisement.

EF Study Subjects

In the SOHFA project, prevalent diabetes was assessed by medication review and fasting blood glucose level, obtained from whole blood samples after at least 12 hours of overnight fasting and measured with the hexokinase method after precipitation of the proteins with trichloroacetic acid Thermo Electron Corp., Vantaa, Finland). A person was considered diabetic if he/she currently used diet or took medication to control blood glucose or if he/she had a fasting blood glucose level of >6.7 mmol/L (120 mg/dL). To assess also the long-time glucose status, HBA1c percent was measured by ion exchange liquid chromatography.

The cases had T2D and family history of T2D. All T2D cases (probands) had at least one additional affected relative, who was a parent, sibling or offspring of the proband. Most of them had more than one additional affected family member. The controls had neither T2D nor family history of T2D. The fasting blood glucose of the controls was 5.5 mmol/L or less and the glycated hemoglobin 5.5% or less.

Age and tobacco smoking were recorded on a self-administered questionnaire checked by an interviewer. HDL fractions were separated from fresh serum by combined ultracentrifugation and precipitation. The cholesterol contents of lipoprotein fractions and serum triglycerides were measured enzymatically. Both systolic and diastolic BPs were measured in the morning by a nurse with a mercury sphygmomanometer. The measuring protocol included three measurements in standing position with 5-minute intervals. The mean of all three measurements were used as SBP and DBP. Body mass index (BMI) was computed as the ratio of weight to the square of height ($kg/m^2$). Waist-to-hip ratio (WHR) was calculated as the ratio of waist circumference (average of one measure taken after inspiration and one taken after expiration at the midpoint between the lowest rib and the iliac crest) to hip circumference (measured at the level of the trochanter major).

The mean age of the cases was 64 years and that of the controls 67 years. Some cases had very low blood glucose, since they had hypoglycemic medication. In spite of this, the average blood glucose and glycated hemoglobin of the cases were higher than that of the controls. Since there was no matching according to obesity, the cases were on the average more obese than the controls.

Ashkenazi Jewish (AJ) Study Subjects

Subjects included in the study were collected in Israel by the physicians in charge in specialized clinics. Subjects were diagnosed with Type II Diabetes Mellitus according to the etiologic classification of Diabetes Mellitus proposed by the International Expert Committee under the sponsorship of the American Diabetes Association on May 1997. We included in the study 200 subjects (82 males and 118 females, mean age 64), each with 3 or more blood relatives of second degree or closer, suffering from T2D.

Matching 200 healthy control subjects (82 males and 118 females, mean age 74) were collected from the Israeli blood bank and elderly patients visiting general practitioners clinics. All subjects were of Ashkenazi Jewish origin. The study was approved by the appropriate ethics committees and participants had signed informed consent forms.

German (GE) and English (UK) Study Subjects

In Germany, cases were sampled from T2D patients from the Hospital of Diabetes and Metabolic Diseases (Karlsburg, Germany) and the diabetes dispensary unit of the Department of Endocrinology of the Emst-Moritz-Amdt University (Greifswald, Germany). The controls were sampled from the non-diabetic examinees of the population based SHIP study cohort (Luedemann et al 2002). Total of 49 cases (24 females and 25 males) and 50 matched healthy controls (24 females and 26 males) from Germany were included in the study.

From England total of 50 cases (31 females and 19 males) and 50 matched healthy controls (31 females and 19 males) were included in the study. The controls were selected from the examinees of the Age and Cognitive Performance Research Centres (ACPRC) volunteer panel, a group of over 6000 older adults who have been previously described in detail (Rabbitt et al, 2004). A cohort of approximately 2000 of these individuals has DNA archived in the Dyne-Steel DNA bank. A group of 456 of these volunteers, residents of Greater Manchester, had previously taken part in a research study in 2001 which included medical history, including that of Diabetes Mellitus, and measurement of $HbA_{1C}$. From the original cohort of 456, a sample of 50 individuals was identified to sex match diabetic cases from Manchester. Each individual had an $HbA_{1C}$ below 5.5% and at telephone interview of family diabetes mellitus history in 2006, reported no evidence of diabetes mellitus in parents or siblings. The University of Manchester research ethics committee approved the study and each individual completed an individual form of consent.

Definition of Cases and Controls for Obesity

Among the 997 T2D study subjects there were 286 obese cases and 286 normal weight controls, which were qualified for the obesity study. From the 572 obesity study subjects 262 were Eastern Finnish (131 cases and 131 controls), 200 were Ashkenazi Jewish 100 (100 cases and 100 controls), 54 were German (27 cases and 27 controls) and 56 were English (28 cases and 28 controls). The cut-off limits for BMI were selected population-specifically so that the number of cases and controls was identical in each of the four study populations (Eastern Finns, Ashkenazi Jews, Germans and English) .The minimum BMI in the cases and the maximum BMI ion the controls are shown in the table below. The cases had BMI of 30 $kg/m^2$ or more (average in EF samples was 35.6, in AJ samples 34.4 and in GE and UK subjects 37.5; BMI of the cases were between 30 and 70). The controls had no previous diagnosis of obesity and their BMI was 27 kg/m or less (average in EF samples was 23.4, in AJ samples 22.8 and in GE and UK subjects 24; BMI of the controls were between 16.6 and 27). Most of the cases had family history of obesity.

Genomic DNA Isolation and Quality Testing

High molecular weight genomic DNA from EF samples was extracted from frozen venous whole blood using standard methods (proteinase K digestion, phenol-chloroform extractions and precipitation) and dissolved in standard TE buffer.

The quantity and purity of each DNA sample was determined by absorbance measurements done with NanoDrop ND-1000 Spectrophotometer (NanoDrop Technologies, Wilmington, Del. USA). A sample was qualified for genome wide scan (GWS) analysis if A260/A280 ratio was ≧1.7. Before GWS analysis the samples were diluted to concentration of 60 ng/μl in reduced EDTA TE buffer (TEKnova, Hollister, Calif., USA).

Genome-Wide Scanning using Illumina's HumanHap300

The whole-genome genotyping of the DNA samples was performed by using Illumina's Sentrix HumanHap300 Bead-Chips and Infinium II genotyping assay. The HumanHap300 BeadChip contained over 317,000 tagSNP markers derived from the International HapMap Project. TagSNPs are loci that can serve as proxies for many other SNPs. The use of tagSNPs greatly improves the power of association studies as only a subset of loci needs to be genotyped while maintaining the same information and power as if one had genotyped a larger number of SNPs.

The Infinium II genotyping with the HumanHap300 Bead-Chip assays was performed according to the "Single-Sample BeadChip Manual process" described in detail in "Infinium™ II Assay System Manual" provided by Illumina (San Diego, Calif., USA). Briefly, 750 ng of genomic DNA from a sample was subjected to whole-genome amplification. The amplified DNA was fragmented, precipitated and resuspended to hybridization buffer. The resuspended sample was heat denatured and then applied to one Sentrix Human-Hap300 beadchip. After overnight hybridization mis- and non-hybridized DNA was washed away from the BeadChip and allele-specific single-base extension of the oligonucleotides on the BeadChip was performed in a Tecan GenePaint rack, using labeled deoxynucleotides and the captured DNA as a template. After staining of the extended DNA, the Bead-Chips were washed and scanned with the BeadArray Reader (Illumina) and genotypes from samples were called by using the BeadStudio software (Illumina).

Infinium II genotyping with the HumanHap300 Bead-Chips were done for 201 EF T2D cases and 200 EF healthy controls, for 200 AJ T2D cases and 197 healthy controls, for 49 German T2D cases and 50 healthy controls and for 50 English T2D cases and 50 healthy controls including the 572 obesity study subjects.

Example 3

Statistical Analyses of the GWS Data of the Obesity and T2D Studies (from Examples 1. and 2.)

Initial SNP Selection for Statistical Analysis

Prior to the statistical analysis, SNP quality was assessed on the basis of three values: the call rate (CR), minor allele frequency (MAF), and Hardy-Weinberg equilibrium (H-W). The CR is the proportion of samples genotyped successfully. It does not take into account whether the genotypes are correct or not. The call rate was calculated as: CR=number of samples with successful genotype call/total number of samples. The MAF is the frequency of the allele that is less frequent in the study sample. MAF was calculated as: MAF=min(p, q), where p is frequency of the SNP allele 'A' and q is frequency of the SNP allele 'B'; p=(number of samples with "AA"-genotype+0.5*number of samples with "AB"-genotype)/total number of samples with successful genotype call; q=1−p. SNPs that are homozygous (MAF=0) cannot be used in genetic analysis and were thus discarded. H-W equilibrium is tested for controls. The test is based on the standard Chi-square test of goodness of fit. The observed genotype distribution is compared with the expected genotype distribution under H-W equilibrium. For two alleles this distribution is $p^2$, $2pq$, and $q^2$ for genotypes 'AA', 'AB' and 'BB', respectively. If the SNP is not in H-W equilibrium it can be due to genotyping error or some unknown population dynamics (e.g. random drift, selection).

Different selection criteria were used for Affymetrix100K (Example 1.) and Illumina300K assays (Example 2.). For Affymetrix100K markers with CR>50%, MAF>1%, and H-W equilibrium Chi-square test statistic<23.93 (the control group) were used in the statistical analysis. For Illumina300K markers with CR>90%, MAF>1%, and H-W equilibrium Chi-square test statistic<27.5 (the control group) were used in the statistical analysis. A total of 100,848 Affymetrix100K SNPs and 315,917 Illumina300K SNPs fulfilled the above criteria.

Single SNP Analysis

Differences in allele distributions between cases and controls were screened for all SNPs. The screening was carried out using the standard Chi-square independence test with 1 df (allele distribution, 2×2 table). SNPs that gave a P-value less than 0.001 (Chi-square with 1 df of 10.23 or more) were considered statistically significant and reported in the tables. Odds ratio was calculated as ad/bc, where a is the number of minor alleles in cases, b is the number of major alleles in cases, c is the number of minor allele in controls, and d is the number of major alleles in controls. Minor allele was defined as the allele for a given SNP that had smaller frequency than the other allele in the control group.

Genotype Analysis

Logistic regression (R-programming language) with three genetic models were tested: additive, recessive and dominance. As an example if the alleles of the SNP are A and C then additive model tests the linear increase in disease risk from genotype AA to AC to CC. In the dominance and recessive model heterozygous genotypes are combined with either AA or CC genotypes.

Haplotype Analysis

The data set was analyzed with a haplotype pattern mining algorithm with HPM software (Toivonen HT et al, 2000). For HPM software, genotypes must be phase known to determine which alleles come from the mother and which from the father. Without family data, phases must be estimated based on population data. We used the HaploRec program (Eronen L et al, 2004) to estimate the phases. For phase-known data HPM finds all haplotype patterns that are in concordance with the phase configuration. The length of the haplotype patterns can vary. As an example, if there are four SNPs and an individual has alleles A T for SNP1, C C for SNP2, C G for SNP3, and A C for SNP4, then HPM considers haplotype patterns that are in concordance with the estimated phase (done by HaploRec). If the estimated phase is ACGA (from the mother/father) and TCCC (from the father/mother) then HPM considers only two patterns (of length 4 SNPs): ACGA and TCCC. A SNP is scored based on the number of times it is included in a haplotype pattern that differs between cases and controls (a threshold Chi-square value can be selected by the user). Significance of the score values was tested based on permutation tests. Several parameters can be modified in the HPM program including the Chi-square threshold value (−x), the maximum haplotype pattern length (−1), the maximum number of wildcards that can be included in a haplotype pattern (−w), and the number of permutation tests in order to estimate the P-value (−p).

Results of the GWS Studies (Examples 1. and 2.)

Table 1 lists the genes that were found to be associated with T2D. Table 2 lists the genes that were found to be associated with obesity or related traits (BMI and subscapular skinfold thickness). The patent ID number and the priority date listed in the tables indicates the Jurilab's patent application number where the particular gene has first been listed and the corresponding filing date. Below is the list of the tables where results of different statistical analysis are presented:

Table 3. SNP markers with the strongest association with T2D in the individual marker analysis. The analysis is based on 102 T2D cases and 92 healthy controls from the Eastern Finnish population.

Table 4. Haplotype genomic regions with the strongest association with T2D in the haplotype sharing analysis (HaploRec+HPM) with 5 SNPs. The analysis is based on 102 T2D cases and 92 healthy controls from the Eastern Finnish population.

Table 5. Haplotypes with the strongest association with T2D based on HaploRec+HPM analysis with 5 SNPs. The analysis is based on 102 T2D cases and 92 healthy controls from the Eastern Finnish population.

Table 6. SNP markers with the strongest association with T2D in the individual marker analysis. The analysis is based on 198 T2D cases and 199 healthy controls from the Eastern Finnish population.

Table 7. Haplotype genomic regions with the strongest association with T2D in the haplotype sharing analysis (HaploRec+HPM) with 5 SNPs. The analysis is based on 198 T2D cases and 199 healthy controls from the Eastern Finnish population.

Table 8. Haplotype genomic regions with the strongest association with T2D in the haplotype sharing analysis (HaploRec+HPM) with 8 SNPs. The analysis is based on 198 T2D cases and 199 healthy controls from the Eastern Finnish population.

Table 9. Haplotypes with the strongest association with T2D based on HaploRec+HPM analysis with 8 SNPs. The analysis is based on 198 T2D cases and 199 healthy controls from the East Finnish population.

Table 10. SNP markers with the strongest association with T2D in the individual marker analysis. The analysis is based on 200 T2D cases and 197 healthy controls from the Ashkenazi Jewish population.

Table 11. SNP markers with the strongest association with T2D in the individual marker analysis. The analysis is based on the combined data of 200 T2D cases and 197 healthy controls from the Ashkenazi Jewish population and 201 T2D cases and 200 healthy controls from the Eastern Finnish population.

Table 12. SNP markers with the strongest association with T2D in the individual marker analysis. The analysis is based on 100 T2D male cases and 101 healthy male controls from the Eastern Finnish population.

Table 13. SNP markers with the strongest association with T2D in the individual marker analysis. The analysis is based on 99 T2D female cases and 99 healthy female controls from the Eastern Finnish population.

Table 14. SNP markers with the strongest association with T2D in the individual marker analysis. The analysis is based on 82 T2D male cases and 82 healthy male controls from the Ashkenazi Jewish population.

Table 15. SNP markers with the strongest association with T2D in the individual marker analysis. The analysis is based on 118 T2D female cases and 115 healthy female controls from the Ashkenazi Jewish population.

Table 16. SNP markers with the strongest association with T2D in the individual marker analysis. The analysis is based on the combined data of 82 T2D male cases and 82 healthy male controls from the Ashkenazi Jewish population and 100 T2D male cases and 101 healthy male controls from the Eastern Finnish population.

Table 17. SNP markers with the strongest association with T2D in the individual marker analysis. The analysis is based on the combined data of 118 T2D female cases and 115 healthy female controls from the Ashkenazi Jewish population and 99 T2D female cases and 99 healthy female controls from the Eastern Finnish population.

Table 18. Haplotype genomic regions with the strongest association with T2D in the haplotype sharing analysis (HaploRec+HPM) with 5 SNPs. The analysis is based on 201 T2D cases and 200 healthy controls from the Eastern Finnish population.

Table 19. Haplotype genomic regions with the strongest association with T2D in the haplotype sharing analysis (HaploRec+HPM) with 5 SNPs. The analysis is based on 200 T2D cases and 197 healthy controls from the Ashkenazi Jewish population.

Table 20. Haplotype genomic regions with the strongest association with T2D in the haplotype sharing analysis (HaploRec+HPM) with 5 SNPs. The analysis is based on the combined data of 200 T2D cases and 197 healthy controls from the Ashkenazi Jewish population and 201 T2D cases and 200 healthy controls from the Eastern Finnish population.

Table 21. Haplotype genomic regions with the strongest association with T2D in the haplotype sharing analysis (HaploRec+HPM) with 8 SNPs. The analysis is based on 200 T2D cases and 197 healthy controls from the Ashkenazi Jewish population.

Table 22. Haplotypes with the strongest association with T2D based on HaploRec+HPM analysis with 8 SNPs. The analysis is based on 200 T2D cases and 197 healthy controls from the Ashkenazi Jewish population.

Table 23. Haplotypes with the strongest association with T2D based on HaploRec+HPM analysis with 5 SNPs. The analysis is based on the combined data of 200 T2D cases and 197 healthy controls from the Ashkenazi Jewish population and 201 T2D cases and 200 healthy controls from the Eastern Finnish population.

Table 24. SNP markers with the strongest association with T2D in the individual marker analysis. The analysis is based on the combined data of 200 T2D cases and 197 healthy controls from the Ashkenazi Jewish population, 201 T2D cases and 200 healthy controls from the Eastern Finnish population, 49 T2D cases and 50 healthy controls from the German population and 50 T2D cases and 50 healthy controls from the English population.

Table 25. SNP markers with the strongest association with T2D in the individual marker analysis. The analysis is based on the combined data of 82 T2D male cases and 82 healthy male controls from the Ashkenazi Jewish population, 102 T2D male cases and 101 healthy male controls from the Eastern Finnish population, 25 T2D male cases and 26 healthy male controls from the German population and 19 T2D male cases and 19 healthy male controls from the English population.

Table 26. SNP markers with the strongest association with T2D in the individual marker analysis. The analysis is based on the combined data of 118 T2D female cases and 115 healthy female controls from the Ashkenazi Jewish population, 99 T2D female cases and 99 healthy female controls from the Eastern Finnish population, 24 T2D female cases and 24 healthy female controls from the German population and 31 T2D female cases and 31 healthy female controls from the English population.

Table 27. SNP markers with the strongest association with T2D in the regression analysis with an additive genotype model. The analysis is based on the combined data of 200 T2D cases and 197 healthy controls from the Ashkenazi Jewish population, 201 T2D cases and 200 healthy controls from the Eastern Finnish population, 49 T2D cases and 50 healthy controls from the German population and 50 T2D cases and 50 healthy controls from the English population.

Table 28. SNP markers with the strongest association with T2D in the regression analysis with a recessive genotype model. The analysis is based on the combined data of 200 T2D cases and 197 healthy controls from the Ashkenazi Jewish population, 201 T2D cases and 200 healthy controls from the Eastern Finnish population, 49 T2D cases and 50 healthy controls from the German population and 50 T2D cases and 50 healthy controls from the English population.

Table 29. SNP markers with the strongest association with T2D in the regression analysis with a dominance genotype model. The analysis is based on the combined data of 200 T2D cases and 197 healthy controls from the Ashkenazi Jewish population, 201 T2D cases and 200 healthy controls from the Eastern Finnish population, 49 T2D cases and 50 healthy controls from the German population and 50 T2D cases and 50 healthy controls from the English population.

Table 30. Haplotype genomic regions with the strongest association with T2D in the haplotype sharing analysis (HaploRec+HPM) with 5 SNPs. The analysis is based on the combined data of 200 T2D cases and 197 healthy controls from the Ashkenazi Jewish population, 201 T2D cases and 200 healthy controls from the Eastern Finnish population, 49 T2D cases and 50 healthy controls from the German population and 50 T2D cases and 50 healthy controls from the English population.

Table 31. Haplotypes with the strongest association with T2D based on HaploRec+HPM analysis with 5 SNPs. The analysis is based on the combined data of 200 T2D cases and 197 healthy controls from the Ashkenazi Jewish population, 201 T2D cases and 200 healthy controls from the Eastern Finnish population, 49 T2D cases and 50 healthy controls from the German population and 50 T2D cases and 50 healthy controls from the English population.

Table 32. SNP markers with the strongest association with obesity in the individual marker analysis. The analysis is based on 59 cases and 83 controls from the Eastern Finnish population that were genotyped with Affymetrix100K genotyping chip.

Table 33. Haplotype genomic regions with the strongest association with obesity in the haplotype sharing analysis (HaploRec+HPM) with 5 SNPs. The analysis is based on 59 cases and 83 controls from the Eastern Finnish population that were genotyped with Affymetrix 100K genotyping chip.

Table 34. Haplotype genomic regions with the strongest association with body mass index in the haplotype sharing analysis (HaploRec+HPM) with 5 SNPs. The analysis is based on 250 subjects from the Eastern Finnish population that were genotyped with Affymetrix110K genotyping chip.

Table 35. Haplotype genomic regions with the strongest association with subscapular skinfold thickness in the haplotype sharing analysis (HaploRec+HPM) with 5 SNPs. The analysis is based on 246 subjects from the Eastern Finnish population that were genotyped with Affymetrix100K genotyping chip.

Table 36. Haplotypes with the strongest association with obesity from HaploRec+HPM analysis with 5 SNPs. The analysis is based on 59 cases and 83 controls from the Eastern Finnish population that were genotyped with Affymetrix100K genotyping chip.

Table 37. SNP markers with the strongest association with obesity in the individual marker analysis. The analysis is based on 132 obese cases and 99 normal controls.

Table 38. Haplotype genomic regions with the strongest association with obesity in the haplotype sharing analysis (HaploRec+HPM) with 8 SNPs. The analysis is based on 132 obese cases and 99 normal controls from the Eastern Finnish population.

Table 39. Haplotypes with the strongest association with obesity based on HaploRec+HPM analysis with 8 SNPs. The analysis is based on 132 obese cases and 99 normal controls from the Eastern Finnish population.

Table 40. SNP markers with the strongest association with obesity in the individual marker analysis. The analysis is based on the combined data of 100 obese cases and 100 healthy controls from the Ashkenazi Jewish population, 131 obese cases and 131 healthy controls from the Eastern Finnish population, 27 obese cases and 27 healthy controls from the German population and 28 obese cases and 28 healthy controls from the English population.

Table 41. Haplotype genomic regions with the strongest association with obesity in the haplotype sharing analysis (HaploRec+HPM) with 5 SNPs. The analysis is based on the combined data of 100 obese cases and 100 healthy controls from the Ashkenazi Jewish population, 131 obese cases and 131 healthy controls from the Eastern Finnish population, 27 obese cases and 27 healthy controls from the German population and 28 obese cases and 28 healthy controls from the English population.

Table 42. Haplotypes with the strongest association with obesity based on HaploRec+HPM analysis with 5 SNPs. The analysis is based on the combined data of 100 obese cases and 100 healthy controls from the Ashkenazi Jewish population, 131 obese cases and 131 healthy controls from the Eastern Finnish population, 27 obese cases and 27 healthy controls from the German population and 28 obese cases and 28 healthy controls from the English population.

Example 4

Replication Study

The replication study included 2573 T2D cases and 2776 normoglycemic control subjects, diagnosed according to the 1997 American Diabetes Association criteria. The T2D cases were recruited at the Sud Francilien hospital or at the CNRS UMR8090 Lille. All cases had family history of T2DM (at least one proband's first degree related with T2DM). MODY, neonatal or mitochondrial diabetes were excluded. The control subjects were obtained from a prospective population-based cohort of middle-aged subjects (N=5153 at baseline). They had fasting blood glucose below 6.1 mmol/L at baseline and during a 9-10 year follow-up (measurements at time 0, 3, 6 and 9 years) and they were free of family history of T2D. Genotyping of the ten SNPs in these samples was carried out with the TaqMan technology (Applied Biosystems). In the Table 43 the results from the replication study are presented.

TABLE 43

Association results of the replication study in 2573 French T2D cases and 2776 French controls.

| SNP | Chr | Position | Gene | Minor Allele | MAF | OR[a] (95% CI) | P-value |
|---|---|---|---|---|---|---|---|
| rs6712932 | 2 | 105204030 | None | G | 0.35 | 1.12 (1.03, 1.21) | 0.008 |
| rs1535435 | 6 | 135798715 | AHI1 | A | 0.10 | 1.29 (1.13, 1.47) | 0.0002 |
| rs9494266 | 6 | 135893266 | LOC441171 | A | 0.10 | 1.31 (1.15, 1.49) | 0.00005 |
| rs942740 | 14 | 90228622 | TTC7B | A | 0.19 | 0.86 (0.78, 0.95) | 0.003 |
| rs1749718 | 14 | 90253080 | TTC7B | A | 0.50 | 0.88 (0.81, 0.95) | 0.001 |

[a]Odds ratios are presented for minor allele vs. major allele.

Example 5

Examples of the Content of the Diagnostic Assays

The score that predicts the probability of T2D may be calculated e.g. using a logistic regression equation: probability of T2D=$1/[1+e(-(-a+\Sigma(b_i*X_i))]$, where e is Napier's constant, Xi are variables related to the T2D, bi are coefficients of these variables in the logistic function, and a is the constant term in the logistic function, and wherein a and bi are preferably determined in the population in which the method is to be used, and Xi are preferably selected among the variables that have been measured in the population in which the method is to be used.

As an example the probability of T2D may be estimated with the model Prob(T2D)=$1/[1+e(-(-a+b_1x_1+b_2x_2+b_3x_3+b_4x_4)]$, where $b_i$'s are coefficients depending on the population and combination of $x_i$'s and for each individual xi is the genotype of rs7903146 (or rs7901695 or rs12255372) and $x_2$-$x_4$ are any combination of the SNPs from the following list of SNPs: rs6712932, rs1535435, rs9494266, rs942740, rs1749718, rs3740878, rs1037909 or $x_1$-$x_4$ are any combination of the SNPs from the following list of SNPs: rs7901695, rs12255372, rs6712932, rs1535435, rs9494266, rs942740, rs1749718, rs3740878, rs11037909. The model may also include additional SNPs from the tables 3-31 or some of the $x_i$'s may be other than SNPs including haplotypes, lifestyle and environmental factors.

The score that predicts the probability of obesity may be calculated e.g. using a logistic regression equation: probability of obesity=$1/[1+e(-(-a+\Sigma(b_i*X_i))]$, where e is Napier's constant, Xi are variables related to the obesity, bi are coefficients of these variables in the logistic function, and a is the constant term in the logistic function, and wherein a and bi are preferably determined in the population in which the method is to be used, and Xi are preferably selected among the variables that have been measured in the population in which the method is to be used.

As an example the probability of obesity may be estimated with the model Prob(obesity)=$1/[1+e(-(-a+b_1x_1+b_2x_2+b_3x_3+b_4x_4)]$, where $b_i$'s are coefficients depending on the population and combination of $x_i$'s and for each individual $x_1$-$x_4$ are any combination of the SNPs from the following list of SNPs: rs1165919, rs1774825, rs1607498, rs13116075, rs1519238, rs17007675, rs2816030, rs3956142, rs11157925. The model may also include additional SNPs from the tables 32-42 or some of the $x_i$'s may be other than SNPs including haplotypes, lifestyle and environmental factors.

Example 6

Identification of Drugs Related to Discovered T2D and/or Obesity Genes

To find out know therapeutic agents related to the T2D and/or obesity related genes listed in tables 1 and 2 of this invention were evaluated using the Ingenuity Pathways Analysis (IPA) application from Ingenuity Systems (Redwood City, Calif., US). With IPA we searched known therapeutic agents agonizing, modulating, binding, inhibiting and/or antagonizing (i) expression of a T2D and/or obesity risk gene, (ii) biological activity and/or function of a T2D and/or obesity risk gene encoded polypeptide, or (iii) biological activity and/or function of a T2D and/or obesity gene related metabolic pathway. We identified a total of 483 therapeutic agents or combinations of therapeutic agents targeting 97 of the genes set forth in tables 1 and 2.

Table 44. Therapeutic agents targeting one or more T2D and/or obesity associated genes set forth in tables 1 and 2 of this invention but are not used to treat T2D or a T2D related condition.

Table 45. Therapeutic agents targeting one or more T2D and/or obesity associated genes set forth in tables 1 and 2 of this invention which are currently used to treat T2D or a T2D related condition or which are associated with drug induced diabetes mellitus.

Table 46. Drug combinations targeting one or more T2D and/or obesity associated genes set forth in tables 1 and 2 of this invention but are not used to treat T2D or a T2D related condition. Each drug combination contains at least one therapeutic agent targeting one or more said T2D and/or obesity associated genes.

Yet in another embodiment of the invention a T2D and/or obesity therapy of this invention comprises a drug combination selected from the table 46. The drug combinations set forth in table 46 are currently used to treat diseases other than T2D or a T2D related condition. However, each said drug combination contains at least one therapeutic agent targeting one or more T2D and/or obesity associated genes disclosed in tables 1 and 2 of this invention so a drug combination selected from the table 46 is useful for prevention and/or treatment of T2D or a T2D related condition.

Implications and Conclusions

We have discovered a total of 1008 T2D associated genes and 644 obesity associated genes, in which any T2D and/or obesity associated biomarkers can be used to predict T2D and/or obesity, and thus these markers can be used to develop molecular diagnostic tests for T2D or a T2D related condition. In addition, we have disclosed a set of 6270 SNP markers predicting T2D and a set of 3066 SNP markers predicting obesity. The markers can also be used as part of pharmacogenetic tests used to predict the efficacy of a T2D therapy and guide the selection of effective and safe treatment for a subject. The genes discovered are also useful in development of novel therapies such as drugs and dietary interventions for T2D or a T2D related condition. The genes and markers of this invention can also be used to screen, identify and test novel antiglycemic agents and compounds.

We disclose 483 known therapeutic agents or their combinations related to T2D and/or obesity genes of this invention. The finding that the disclosed agents include agents currently used for treating T2D and/or obesity such as different types of insulin, acarbose, and benzphetamine provides support that also the disclosed agents which are not used to treat T2D or a T2D related condition are useful for developing novel therapies for treating T2D or a T2D related condition. This also provides further evidence for the concept that any gene of the present invention set forth in tables 1 and 2 is a potential target for the development of new therapies for the treatment of T2D and/or obesity or a related condition.

While this invention has been particularly shown and described with reference to preferred embodiments thereof, it will be understood by those skilled in the art that various changes in form and details may be made therein without departing from the spirit and scope of the invention as defined by the appended claims.

REFERENCES

Alberti K G. 1998. Impaired glucose tolerance: what are the clinical implications? Diabetes Res Clin Pract. 40 Suppl: S3-8.

Altshuler D et al. 2000. The common PPARgamma Pro22Ala polymorphism is associated with decreased risk of type 2 diabetes. Nat. Genet. 26:76-80.

American Diabetes Association 2003. Report of the Expert Committee on the Diagnosis and Classification of Diabetes Mellitus. Diabetes Care 26:S5-S20.

American Obesity Association (AOA) 2006. Available at: http://www.obesity.org/ Bailey S J et al. 2007. Glucose-dependent regulation of gamma-aminobutyric acid (GABA A) receptor expression in mouse pancreatic islet alpha-cells. Diabetes. 56(2):320-7.

Bajaj M, Defronzo R A. 2003. Metabolic and molecular basis of insulin resistance. J Nucl Cardiol. 10(3):311-23.

Barosso I et al. 2006. Meta-analysis of the Gly482Ser variant in PPARGC1A in type 2 diabetes and related phenotypes. Diabetologia 49:501-505.

Burton B T and Foster W R 1985. Health implications of obesity: an NIH Consensus Development Conference. J. Am. Diet. Assoc. 85:1117-21.

Deeb SS et al. 1998. A Pro12Ala substitution in PPAR-gamma2 associated with decreased receptor activity, lower body mass index and improved insulin sensitivity. Nat. Genet. 20:284-87.

Eronen L et al. 2004. A Markov chain approach to reconstruction of long haplotypes. Pac Symp Biocomput.: 104-15.

Gloyn A L et al. 2001. Association studies of variants in promoter and coding regions of beta-cell ATP-sensitive K-channel genes SUR1 and Kir6.2 with Type 2 diabetes mellitus (UKPDS 53). Diabetes Med. 18:206-12.

Gloyn A L et al. 2003. Large-scale association studies of variants in genes encoding the pancreatic {beta}-cell KATP channel subunits Kir6.2 (KCNJ11) and SUR1 (ABCC8) confirm that the KCNJ 11 E23K variant is associated with type 2 diabetes. Diabetes 52:568-72.

Grant S F A. et al. 2006. Variant of transcription factor 7-like 2 (TCF7L2) gene confers risk of type 2 diabetes. Nat. Genet. 38:320-232.

Hani E H et al. 1998. Missense mutations in the pancreatic islet beta cell inwardly rectifying K+ channel gene (KIR6.2/BIR): a meta-analysis suggests a role in the polygenic basis of Type II diabetes mellitus in Caucasians. Diabetologia 41:1511-15.

Hara K et al. 2000. The Pro12Ala polymorphism in PPAR gamma2 may confer resistance to type 2 diabetes. Biochem. Biophys. Res. Commun. 271:212-16.

Kaiser N et al. 2003. Glucotoxicity and beta-cell failure in type 2 diabetes mellitus. J Pediatr Endocrinol Metab. 16(1):5-22.

Kwok P-Y 2001. Methods for genotyping single nucleotide polymorphisms. Ann Rev Genomics Hum Genet. 2:235-258.

Ligon B et al. 2007. Regulation of pancreatic islet cell survival and replication by gamma-aminobutyric acid. Diabetologia. 50(4):764-73.

Luedemann J et al. 2002. The association between behavior dependent cardiovascular risk factors and asymptomatic carotid atherosclerosis in a general population. Stroke 33: 2929-2935.

Mori H et al. 2001. The Pro12→Ala substitution in PPAR-gamma is associated with resistance to development of diabetes in the general population: possible involvement in impairment of insulin secretion in individuals with type 2 diabetes. Diabetes 50:891-94.

Mosby's Drug Consult, 13th Edition, J Med Chem 1973 12 1;16(12):1340-6.

Mutch D M and Clement K 2006. Unraveling the genetics of human obesity. PLOS Genetics 2:1956-1963.

Nielsen P E et al. 1991. Sequence-selective recognition of DNA by strand displacement with a thymine-substituted polyamide. Science 254:1497-500.

Pijl H. 2003. Reduced dopaminergic tone in hypothalamic neural circuits: expression of a "thrifty" genotype underlying the metabolic syndrome?

Porte D, Jr., Kahn SE 2001. beta-cell dysfunction and failure in type 2 diabetes: potential mechanisms. Diabetes. 50 Suppl 1:S160-3.

Rabbitt P et al. 2004. The University of Manchester Longitudinal Study of Cognition in Nomral Healthy Old Age, 1983 through 2003. Aging, Neuropsychol. Cogn. 11: 245-270.

Ristow M. 2004. Neurodegenerative disorders associated with diabetes mellitus. J Mol Med. 82:510-529

Saxena R et al. 2006. Common single nucleotide polymorphism in TCF7L2 are reproducibly associated with type 2 diabetes and reduce the insulin response to glucose in nondiabetic individuals. Diabetes 55:2890-2895.

Scheen A J 2003. Pathophysiology of type 2 diabetes. Acta Clin Belg. 58:335-41.

Stumvoll M et al.2005. Type 2 diabetes: principles of pathogenesis and therapy. Lancet. 365(9467): 1333-46.

Stunkard A J et al. 1986. An adoption study of human obesity. N Engl J Med 314:193-8.

Syvänen A-C 2001. Accessing genetic variation: Genotyping single nucleotide polymorphisms. Nature Reviews Genetics 2:930-942.

Toivonen H T et al. 2000. Data mining applied to linkage disequilibrium mapping. Am. J. Hum. Genet. 67:133-45.

Tsuchiya T et al. 2006. Association of the calpain-10 gene with type 2 diabetes in Europeans: results of pooled and meta-analyses. Mol. Genet. Metab. 89:174-184.

Tuomilehto J, Lindstrom J, Eriksson J G, et al. 2001. Prevention of type 2 diabetes mellitus by changes in lifestyle among subjects with impaired glucose tolerance. N Engl J Med. 344(18): 1343-50.

Warram J H, Martin B C, Krolewski A S, Soeldner J S, Kahn C R. 1990. Slow glucose removal rate and hyperinsulinemia precede the development of type II diabetes in the offspring of diabetic parents. Ann Intern Med.113(12): 909-15.

Weyer C, Bogardus C, Mott DM, Pratley RE. 1999. The natural history of insulin secretory dysfunction and insulin resistance in the pathogenesis of type 2 diabetes mellitus. J Clin Invest. 104(6):787-94.

Wolf A M and Colditz G A 1998. Current estimates of the economic cost of obesity in the United States. Obes Res. 6:97-106.

World Health Organization and the International Diabetes Federation. 2004. Diabetes Action Now booklet. http://www.who.int/diabetes/actionnow/booklet/en (Accessed 02.07.04)

World Health Organization. 2004. Diabetes Mellitus fact sheet. http:/www.who.int/mediacentre/factsheets/fs138/en (Accessed 02.07.04).

WO2006/040409. Method and kit for detecting a risk of acute myocardial infarction.

The invention claimed is:

1. A method for determining an increased risk of type 2 diabetes, in a human subject comprising:
   a) providing a biological sample taken from the subject;
   b) testing the sample for the presence of the A allele at position rs1749718 in said sample,
   wherein the presence of the A allele is associated with an increased risk of type 2 diabetes.

2. The method according to claim 1, further comprising testing the sample for the presence of at least one of the alleles selected from the group consisting of the A allele at position rs6712932, the A allele at position rs1535435, the A allele at position rs9494266, and the A allele at position rs942740.

3. The method according to claim 1, further comprising testing the sample for the presence of at least one of the alleles selected from the group consisting of the A allele at position rs2591797, the A allele at position rs7002832, the G allele at position rs911946, the G allele at position rs12531570, the A allele at position rs10151259, the A allele at position rs4383389, the A allele at position rs7581414, the A allele at position rs4446815 and the C allele at position rs4417767.

* * * * *